United States Patent
Shindelman (12)

(10) Patent No.: US 6,306,616 B1
(45) Date of Patent: *Oct. 23, 2001

(54) ADSORPTION TYPE CONFIRMATORY ASSAYS

(75) Inventor: Jeffrey E. Shindelman, Concord, CA (US)

(73) Assignee: Microgenics Corporation, Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/049,464

(22) Filed: Mar. 27, 1998

(51) Int. Cl.$^7$ .................... G01N 33/533; G01N 33/534; G01N 33/545

(52) U.S. Cl. .................. 435/7.93; 435/7.94; 436/531; 436/546; 436/815

(58) Field of Search ................. 435/7.93, 7.94; 436/546, 815, 531

(56) References Cited

U.S. PATENT DOCUMENTS

| | | | |
|---|---|---|---|
| 3,856,469 | 12/1974 | Schneider et al. . | |
| 4,477,346 | 10/1984 | Dickinson et al. . | |
| 4,708,929 | 11/1987 | Henderson | 435/188 |
| 4,722,889 | 2/1988 | Lee et al. | 435/188 |
| 4,843,020 | 6/1989 | Woodford | 436/518 |
| 4,952,336 | 8/1990 | Brynes et al. . | |
| 5,064,755 | 11/1991 | Howard, Jr. et al. | 435/7.36 |
| 5,101,015 | 3/1992 | Brynes et al. | 436/501 |
| 5,248,791 | 9/1993 | Brynes et al. | 549/223 |
| 5,296,354 | 3/1994 | Simon et al. | 435/7.92 |
| 5,308,775 | 5/1994 | Donovan et al. | 436/518 |
| 5,328,828 | 7/1994 | Hu et al. | 436/7.92 |
| 5,354,693 | 10/1994 | Brynes et al. | 436/537 |
| 5,470,997 | 11/1995 | Buechler et al. | 436/544 |
| 5,518,887 | 5/1996 | Parsons et al. | 435/7.1 |
| 5,573,955 | 11/1996 | Khanna et al. | 435/7.1 |

FOREIGN PATENT DOCUMENTS

| | | |
|---|---|---|
| 0353614 | 2/1990 | (EP) . |
| 0399184 | 11/1990 | (EP) . |
| 0 371 253 | 9/1995 | (EP) . |
| 0816364 | 1/1998 | (EP) . |
| 0820984 | 1/1998 | (EP) . |
| 2 279 076 | 12/1994 | (GB) . |
| WO 94/24559 | 10/1994 | (WO) . |
| WO 97/19100 | 5/1997 | (WO) . |

OTHER PUBLICATIONS

W. Ratcliffe et al, Clin, Chem., 23/2, 169–174 (1977).*

D'Nicuola et al., "Evaluation of six commercial amphetamine and methamphetamine immunoassays for cross–reactivity to phenylpropanolamine and ephedrine in urine" *J. Anal. Toxicol.* (1992) 16:211–213.

ElSohly et al., "A procedure for eliminating interferences from ephedrine and related compounds in the GC/MS analysis of amphetamine and methamphetamine" *J. Anal. Toxicol.* (1992) 16:109–111.

Hu et al., "EMIT® II LSD assay on the SYVA–30R analyzer" *Clin Chem.* (1996) 42(S6):S219–220 (Abstract No. 517).

Paul et al., "Amphetamine as an artifact of methamphetamine during periodate degradation of interfering ephedrine, pseudoephedrine, and phenylpropanolamine: An improved procedure for accurate uantitation of amphetamines in urine" J. Anal Toxicol. (1994) 18:331–336.

Spiehler et al., "Elimation of ephedrine and pseudoephedrine cross–reactivity in the coat–a–count methamphetamine radioimmunoassay" *J. Anal. Toxicol.* (1993) 17:125–126.

Webb et al., "The analysis of lysergide (LSD): The development of novel enzyme immunoassay and immunoaffinity extraction procedures together with an HPLC–MS confirmation procedure" *J. Forensic Sciences* (1996) 41:938–946.

Product insert: "Amphetamine/methamphetamine II" TRX®/TRXFLX®, Abbott Laboratories (1996).

Product insert: "Amphetamines" COBAS INTEGRA, Roche Diagnostics, Version 2.0 (1996).

Product insert: "Antibody to Hepatitis B surface antigen REAC–801 confirmatory test" SORIN BIOMEDICA, INCSTAR CORP. (1994).

Product insert: "CEDIA® DAU AMPHETAMINES" Boehringer Mannheim (1997).

Product insert: "Monoclonal amphetamine/methamphetamine assay" Emit® II, Behring Diagnostics (1997).

LSD–Qualitative CEDIA® insert.

Owens et al., "Antibodies against arylcyclohexylamines and therir similarities in binding specificity with the phencyclidine receptor" *J. Pharm. Exp. Ther.* (1988) 246:472–478.

Derwent World Patent Index, English–language summary of EP 0820984.

* cited by examiner

*Primary Examiner*—Mary E. Ceperley
(74) *Attorney, Agent, or Firm*—Wood, Herron & Evans, L.L.P.

(57) ABSTRACT

The invention relates to an assay system for the improved detection of analytes, and the ability to distinguish them from cross-reacting substances. Samples giving a positive reaction in a direct assay test are treated with a neutralizing antibody that inhibits reactivity of the true analyte, but not the interfering substance. In adsorption type confirmatory assays, the neutralizing antibody is provided in an amount sufficient to adsorb the analyte but not all of the interfering substance. When retested in an immunoassay, the neutralized sample gives a negative result if it originally contained the true analyte. Samples giving a positive reaction in both the direct and confirmatory tests are marked as containing an interfering substance. The confirmatory assay easily distinguishes the true analyte and reduces the rate of false positives, even when the interfering substance is unknown and present at high concentration.

26 Claims, 5 Drawing Sheets

ADSORPTION TYPE CONFIRMATORY ASSAYS

TECHNICAL FIELD

This invention relates generally to the field of the detection of drugs and drug metabolites in biological samples. More specifically, it provides a system for confirming the presence of a particular analyte in a sample potentially containing interfering substances.

BACKGROUND

The ability to perform rapid screening tests in diagnostic medicine has been considerably facilitated by the evolving art of immunoassay. Antibodies can be raised that have exquisite specificity and sensitivity for small molecules of diagnostic interest. In combination with other reagents that have a separating or labeling function, specific antibodies can be used as part of a rapid screening test for the presence of the small molecule in a clinical sample.

Small molecules that can be measured in this way include hormones, natural metabolites, and prescription drugs. Of increasing interest is the detection of substances of abuse, particularly the inappropriate voluntary use of recreational drugs. Substances of abuse include canabinoids, tranquilizers such as barbiturates, stimulants such as amphetamines, hallucinogenic alkaloids such as cocaine and lysergic acid diethylamide (LSD), and anabolic steroids.

U.S. Pat. Nos. 4,952,336 and 5.354,693 and E.P. Patent 371,253-B relate to the detecting of analytes in the amphetamine class in an assay using fluorescent tracers and antibodies raised against amphetamine derivatives. In U.S. Pat. No. 5,328,828, an assay method is recited in which the sample is combined with reagent antibodies and protein conjugates for both amphetamine and methamphetamine. Diagnostic kits for measuring amphetamine class compounds are available commercially using the CEDIA® DAU technology of Boehringer Mannheim Corp., the fluorescence polarization immunoassay (FPIA) technology of Abbott Laboratories, the EMIT®=0 II technology of Behring Diagnostics, the COBAS® INTEGRA technology of Roche Diagnostics, and the COAT-A-COUNT® radioassay technology of Diagnostic Products Corporation.

Radioimmunoassay kits for LSD are sold in the ABUSCREEN® product line by Roche and the COAT-A-COUNT® product line . International patent application PCT/US 96/19266 provides reagents and procedures for the detection and measurement of LSD in an enzyme immunoassay. A diagnostic kit for LSD based on this technology is commercially available in the CEDIA® DAU product line. More recently, other enzyme-type immunoassays for LSD and related compounds have been developed (Hu et al., Clin. Chem. (1996) 42:S219; Webb et al., J. Forensic Sciences (1996) 41:938).

Because of the possible legal implications of a positive test result, it is important that a positive immunoassay test for a substance of abuse be verified. The touchstone verification test for small molecule drugs is mass spectroscopy—particularly when combined with gas or liquid chromatography (GC/MS or LC/MS), or tandem mass spectrometry (GC/MS/MS or LC/MS/MS). These secondary tests are complex, require expensive instrumentation and highly trained personnel, and therefore are very expensive as compared to the initial screening test. Any reduction in the proportion of false positives selected for verification reduces the overall costs of drug screening.

For the problem of cross-reactivity in commercially available amphetamine assays, see D'Nicuola et al., J. Anal. Toxicol. (1992) 16:221. A major cause of false positives in the screening immunoassay is that the detecting antibody for the analyte cross-reacts with an interfering substance that is present in the samples. Accordingly, certain technologies have been developed with a view to reducing the frequency of false positives due to cross-reactivity.

Strategies for reducing false positives in assays for small molecule drugs have been principally oriented at either improving the specificity of the detecting antibody, or neutralizing the effect of the interfering substance in the sample.

U.S. Pat. No. 3,856,469 relates to the removal of β-hydroxyamine compounds from samples to be tested for amphetamine, by treating with aqueous periodate under mildly basic conditions. Modifications of the periodate treatment method have been described for reducing interference by ephedrine, pseudoephedrine, and phenylpropanolamine. See Elsohly et al., J. Anal. Toxicol. (1992) 16:109; Spiehler et al., J. Anal. Toxicol. (1993) 17:125; and Paul et al., J. Anal. Toxicol. (1994) 18:331. U.S. Pat. No. 5.573,955 describes reducing tyramine interference in amphetamine immunoassays by treating with tyramine oxidase.

U.S. Pat. No. 4,843,020 relates to a method for detecting tetrahydrocannabinol (THC) in human urine by precipitating out any melanin that might be present by treating with nitroferricyanide. U.S. Pat. No. 4,477,346 relates to a method for removing interfering substances in theophylline assays, particularly caffeine. The sample to be tested is pre-treated by liquid-liquid extraction using hydrophobic, macroreticular resin slurried in a protic solvent.

U.S. Pat. No. 5,518,887 relates to competition assays using an insolubilized analog of the substance to be measured. Two different detecting antibodies are used, one of which is selected to have less cross-reactivity for the interfering substance. The disclosure proposes that the method be used to distinguish between phencyclidine (PCP) and structurally related substance, particularly 2-ethylidene-1,5-dimethyl-3,3-diphenylpyrrolidine (EDDP), a methadone metabolite. In the presence of the true analyte, the binding of both antibodies to the insolubilized analog is inhibited, whereas the interfering substance is proposed to have less effect on the antibody that is more specific. Thus, positive inhibition of both antibodies would confirm the presence of the true analyte.

Strategies have also been developed for distinguishing between related proteins. Several of these strategies involve the use of several different antibodies in the analysis, relying on a difference in epitopes attributable to amino acid sequence differences between the target analyte and the potentially cross-reacting substance.

U.S. Pat. No. 4,722,889 relates to a solid-phase sandwich-type immunoassay for human chorionic gonadotropin (hCG). A scavenger antibody is included in the reaction mixture that prevents cross-reacting protein hormones from reacting with the capture or detecting antibody.

U.S. Pat. No. 5,296,354 relates to a competition-type immunoassay that is intended to distinguish Angiotensin II from any Angiotensin III that may be present in the sample. Detection of the analyte occurs via an inhibition of the reaction between an anti-Angiotensin II antibody and a labeled Angiotensin II reagent. The reaction mixture includes an antibody more specific for Angiotensin III, which is intended to prevent any Angiotensin III from inhibiting the reaction between the anti-Angiotensin II and the labeled reagent.

U.S. Pat. No. 5,064,755 is directed to a two-site confirmatory assay. The disclosure relates a method for confirming the presence in a sample of a Chlamydia antigen, which is a complex multi-epitope antigen with variant subspecies. The confirmatory assay involves comparing the results of two different tests. The first test involves developing the sample with a detecting antibody specific for Chlamydia antigen. The second test involves treating a duplicate sample with a confirmatory antibody before the detecting antibody. A predetermined decrease in signal resulting from pretreatment with the confirmatory antibody confirms the presence of the antigen in the sample. The second antibody is chosen so as to be capable of binding a second epitope on the Chlamydia and thereby prevent the binding of the first antibody.

U.S. Pat. No. 5,308,755 is directed to an assay device for concurrently detecting an analyte and confirming the test result. The exemplary device has two fluid-flow pathways, and is illustrated for use in detecting hepatitis B surface antigen (HBsAg). The first pathway contains a binding member (such as anti-HBsAg) which participates in forming an immobilized labeled complex if analyte is present in the test sample. The second pathway contains in addition a mobile confirmatory reagent (such as anti-HBsAg) which inhibits the binding of the immobilized labeled complex. The amount of labeled analyte complex immobilized in the first pathway is related to the presence of analyte in the sample, which is confirmed if the confirmatory reagent prevents the formation of the immobilized labeled complex.

A neutralization assay for confirming HBsAg in a sample is manufactured by Sorin Biomedica (Italy) and distributed in the U.S. by Incstar Corporation. The assay is described in the Instruction Manual for the REAC-801 Confirmatory Test. In the direct determination, HBsAg is captured using a first antibody on a solid phase, and developed using a labeled second antibody that reacts against a second epitope on the HBsAg. The confirmatory test involves treating the captured HBsAg with an unlabeled, neutralizing antibody before adding the labeled antibody. The neutralizing antibody is specific for HBsAg, and blocks subsequent binding of the labeled antibody to its specific epitope on HBsAg. If the signal of the neutralized sample is significantly lower than the signal of the non-neutralized sample, the presence of HBsAg in the sample is confirmed.

DISCLOSURE OF THE INVENTION

The present invention provides a system for the improved detection of analytes, and the ability to distinguish them from cross-reacting substances. Samples giving a positive reaction in a direct immunoassay test are treated with a neutralizing antibody that inhibits reactivity of the true analyte, but not the interfering substance. Thus samples giving a positive reaction in the direct test but decreased reaction in the confirmation test are marked as containing the true analyte. Samples giving a positive reaction of roughly equivalent magnitude in both the direct and confirmation test are marked as containing an interfering substance.

Certain types of confirmatory assays described in this disclosure are classified as bidirectional antibody type confirmatory assays. Certain types of confirmatory assays described in this disclosure are adsorption type confirmatory assays.

In adsorption type confirmation assays, the sample is treated with an amount of neutralizing antibody that is sufficient to remove or neutralize the analyte but not all the interfering substance from the sample, or otherwise prevent its binding to the detecting antibody. In particular embodiments of this type of assay, the neutralizing antibody is provided in an insolubilized form, and the detection step is performed after removal or neutralization of the analyte.

Embodiments relating to adsorption type confirmation assay include reagent sets and kits for distinguishing between an analyte and an interfering substance. One such embodiment comprises a detecting antibody for the analyte, and a neutralizing antibody for the analyte. The neutralizing antibody preferentially binds the analyte in comparison with the interfering substance. The neutralizing antibody is preferably either aliquoted in an amount sufficient to remove the analyte but not all the interfering substance from the sample, or a written indication is provided as to the amount required. The set of reagents also typically comprises a competitive binding compound, with the property that the detecting antibody binds the hapten derivative in a manner that is specifically inhibitable by the analyte and the interfering substance. An exemplary competitive binding compound is a hapten derivative, such as a hapten-protein conjugate or a hapten labeled with a radioisotope or fluorochrome.

Other embodiments of the invention are reagents and kits for adapting an assay to permit distinguishing the analyte from an interfering substance, comprising a neutralizing antibody. The assay is conducted using a detecting antibody and a competitive binding compound, and the neutralizing antibody provided in this embodiment performs in the assay according to the properties already outlined. Typically, written instructions for conducting the confirmatory assay are included with the kit.

Further embodiments of the invention are assay methods. One such embodiment is an assay method for distinguishing between a small molecule analyte and an interfering substance in a sample. A direct assay is conducted to determine the amount of analyte and/or interfering substance in the sample. The same sample or a duplicate is treated with a neutralizing antibody in an amount sufficient to remove the analyte but not the potential interfering substance, and an assay is conducted on the treated sample. The amount detected is then compared between the treated and untreated sample.

Another such embodiment is an assay method for determining an analyte in a sample. A reaction mixture is prepared, comprising the sample, a detecting antibody, and a competitive binding compound, wherein the detecting antibody binds the hapten derivative in a manner that is specifically inhibitable by the analyte. The amount of the detecting antibody bound to the competitive binding compound is measured. To conduct the confirmation part of the test, the same sample is treated with a neutralizing antibody, or else a duplicate sample is treated with a neutralizing antibody before, during or after the direct test. The neutralizing antibody prevents the analyte but not all the interfering substance in the sample from being available to bind the detecting antibody when an assay is conducted on the treated sample. The results from the direct and the confirmatory test are then compared. The presence of true analyte is confirmed if there is a significant effect on the result due to use of the neutralizing antibody.

These technologies are especially appropriate for use on small molecule drugs, such as substances of abuse and their metabolites. Particular small molecules of interest include amphetamines, LSD, and their respective metabolites. Exemplary detecting and neutralizing antibodies for determining substances of the amphetamine class are raised against amphetamine derivative linked to a carrier through a position in the phenol ring, and through the alkyl amine group in either order. Exemplary detecting and neutralizing antibodies for determining substances of the LSD class are raised against LSD derivative linked to a carrier through the indole ring, and through the alkyl amide group.

The technology can be applied to immunoassay detection methods, including but not limited to homogeneous assay systems, such as those involving an enzyme or fluorescent marker in the detection system.

The lower graphs compare the results of the direct assay (left) with the assay adapted to confirm the presence of an amphetamine (right), using a neutralizing antibody specific for both amphetamine and methamphetamine. The neutralizing antibody is specific for the analyte but not the hapten conjugate with which the analyte competes. It neutralizes the true analyte, thereby suppressing the subsequent enzyme signal.

Figure 2:
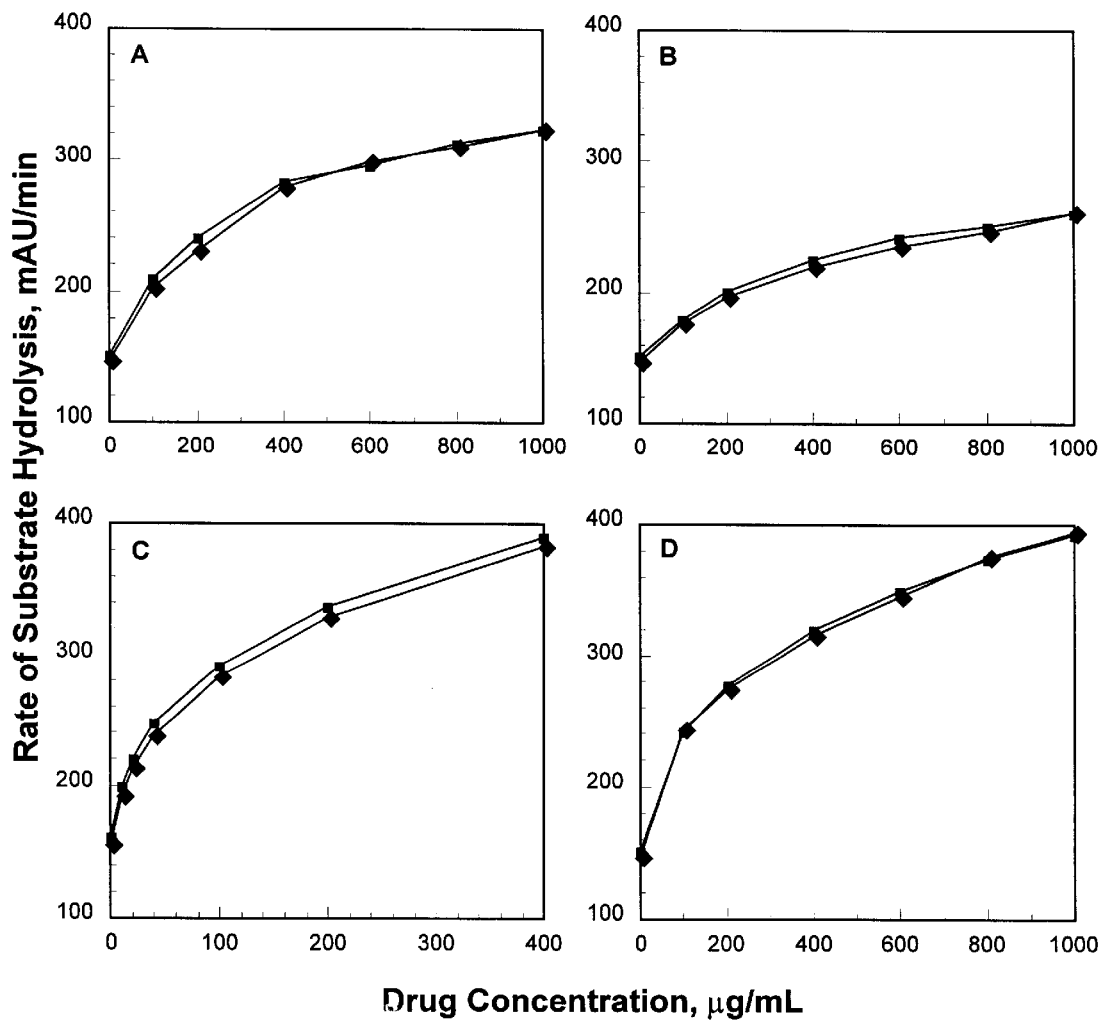

FIG. 2 is a series of four graphs illustrating the results of the amphetamine confirmation assay for samples spiked with several potential interfering substances. The samples were tested in the absence (♦) and presence (■) of the neutralizing antibody. Panel A: pseudoephedrine; Panel B: phenylpropanolamine: Panel C: phentermine; Panel D: tyramine. The neutralizing antibody does not eliminate enzyme signal that is due to interfering substance.

Figure 3:
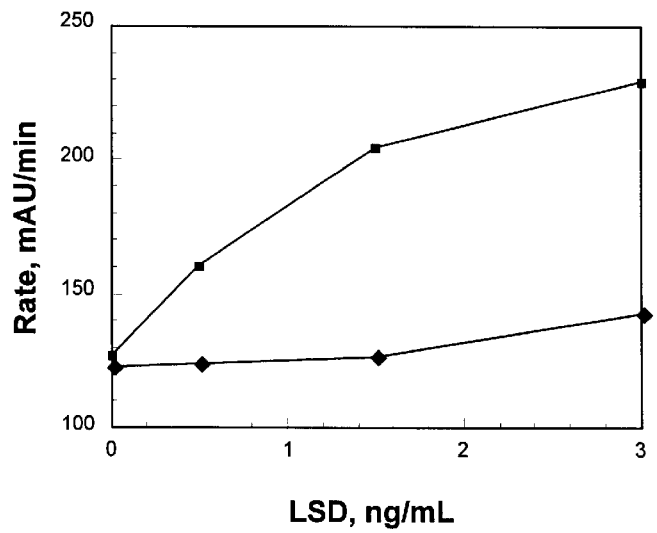
Figure 3:
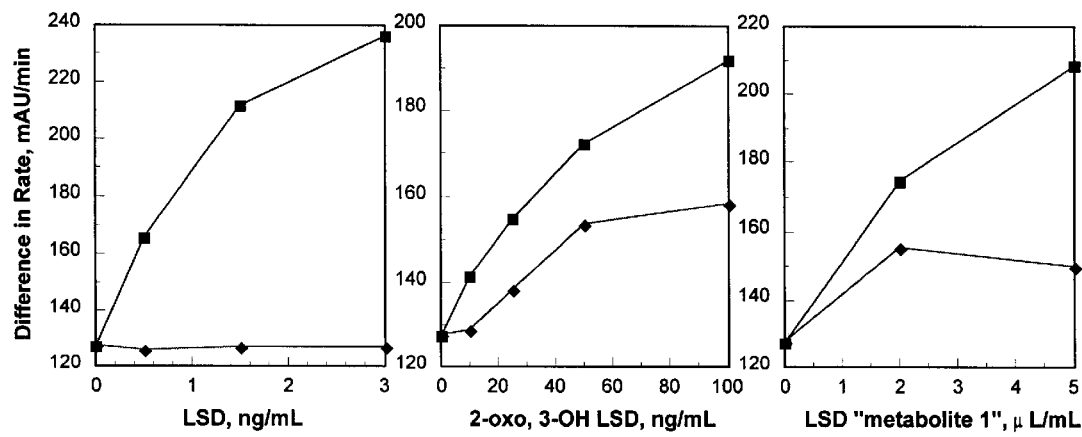

FIG. 3 is a series of four graphs illustrating an adsorption-type confirmation assay for LSD. The upper graph shows the results of a CEDIA® DAU LSD assay in the direct test (■); or after pretreatment of the sample with the neutralizing antibody (♦). In this case, the neutralizing antibody is insolubilized, and removes the analyte from the portion of the sample, which is then tested using the detecting antibody. Elimination of the true analyte again suppresses the subsequent enzyme signal.

The lower three graphs compares the results of the direct (■) and confirmation (♦) test for LSD (Left Panel), 2-oxo-3-hydroxy LSD (Center Panel) or a partially purified preparation containing a mixture of the putative LSD metabolites 13-hydroxy LSD glucuronide and 14-hydroxy LSD glucuronide (Right Panel).

Figure 4:
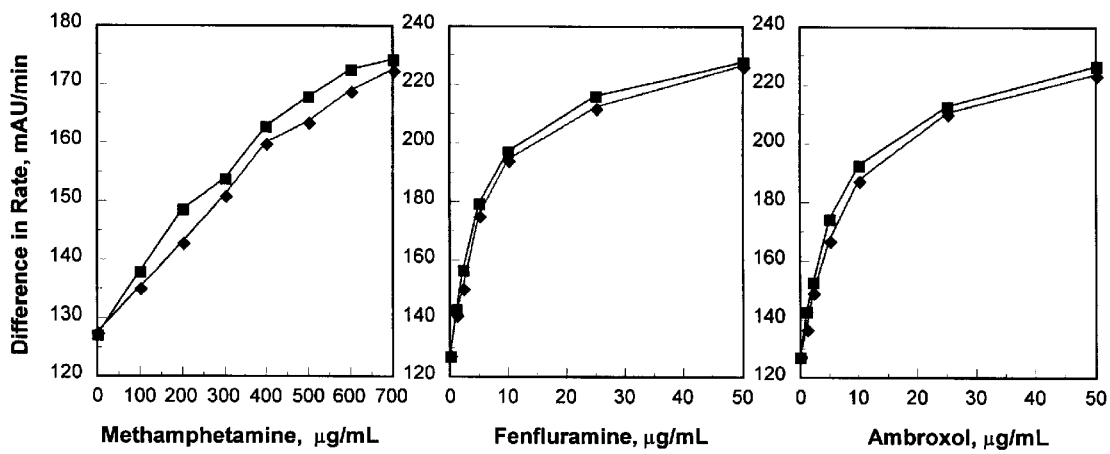

FIG. 4 is a series of three graphs comparing the results of the direct (■) and confirmation (♦) test for LSD for samples spiked with the following potential interfering substances: Left Panel: methamphetamine: Center Panel: fenfluramine; Right Panel: ambroxol.

Figure 5:
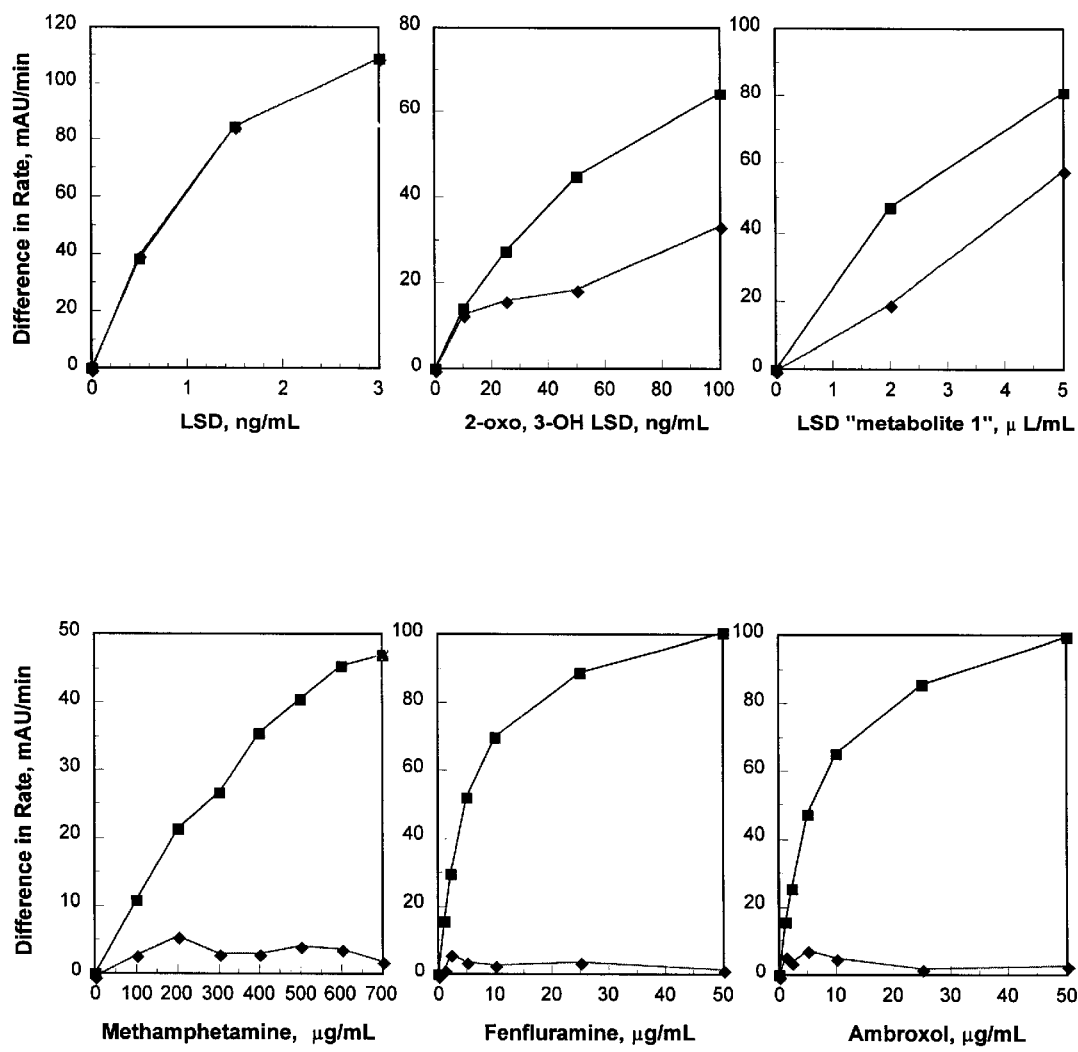

FIG. 5 is a series of six graphs in which the results from FIGS. 3 and 4 are displayed as relative rates. (■) ΔRate 1 (difference between direct test and baseline); (♦) ΔRate 2 (difference between confirmation test and direct test). Upper graphs (left to right): LSD, 2-oxo-3-hydroxy LSD, and hydroxy LSD glucuronides. Lower (graphs (left to right): methamphetamine, fenfluramine, and ambroxol.

DETAILED DESCRIPTION

The present invention is directed to reagents and methods for detecting or confirming the presence of an analyte in a test sample. The analyte is distinguished from one or more cross-reacting interfering substances that may be present in the sample, either as an alternative to or in combination with the analyte.

Immunoassays for small molecule drugs are especially susceptible to the problem of cross-reactivity. In screening urine samples for drugs of abuse, some samples test positive by immunoassay but fail to confirm by GC/MS. For example, during allergy season, 95 to 98% of samples testing positive for amphetamine can be negative in GC/MS. Even a low percentage of false positives can be a problem when the frequency of abuse is low, such as for LSD.

As described in the background section, previous strategies for reducing false positives in assays for small molecule drugs have been principally oriented at either improving the specificity of the detecting antibody, or neutralizing the effect of the interfering substance in the sample. These approaches require prior knowledge of the identity of the interfering substance, and presume that the interfering substance can be neutralized or distinguished away so as not to interfere with measurement of the analyte.

Particularly for small molecule drugs, both of these presumptions are problematic. First, cross-reactivity between chemical structures is not entirely predictable, especially when using monoclonal antibodies. Substances that are present in over-the-counter cold remedies and other mass consumer products may interfere in an immunoassay for a substance of abuse, even where there is no obvious structural similarity between them. Second, the molar concentration of the interfering substance can be several orders of magnitude above the threshold for a positive drug test. A cross-reactivity of even just one percent or less can generate an abundance of false positive results. For example, the test range for LSD in urine is about 0.1 to 5 ng/ml, whereas potentially interfering drugs such as acetaminophen fluoxetine, ibuprofen, cimetidine, and chlorpromazine, can be present in the sample at concentrations of 10 to 2,000 $\mu$g/ml. Even though the cross-reactivity of the detecting antibody may be as low as 0.0003% to 0.01% (Example 7), these substances can cause a substantial number of false positives in a standard LSD immunoassay.

The materials and methods of this invention provide an improved approach for distinguishing a test analyte from interfering substances in an immunoassay. Rather than trying to remove or neutralize the interfering substance, the invention is aimed at removing or neutralizing the true analyte, and retesting the sample for the interfering substance. The advantages of this invention include the following features:

In principle, the approach is suitable in any immunoassay for small molecule analytes, including monovalent haptens It is not necessary to know in advance the nature of the interfering substance The approach is readily implemented in automated homogeneous assays. In some embodiments of the invention, the neutralizing antibody can be added directly to the reaction mixture, without a separation step The confirmation test guards simultaneously against a wide range of potential interfering substances The test is able to distinguish the analyte even in a multi-fold excess of the interfering substance In many embodiments of the invention, the neutralizing antibody in the confirmation part of the test need not be more specific for the analyte than the detecting antibody This last feature is particularly counterintuitive: since the purpose of the neutralizing antibody is to distinguish multiple compounds that all react with the detecting antibody, it would seem that the neutralizing antibody would have to be even more specific. But this is not the case. This disclosure teaches several ways in which a neutralizing antibody can be set up to differentiate between the analyte and the interfering substance, even when its cross-reactivity profile is no better than that of the detecting antibody.

Non-limiting illustrations are provided in this disclosure of diagnostic-grade confirmatory assays for amphetamines and for LSD.

The illustrations provide examples with particular features, described as bidirectional antibody type assays, and adsorption type assays. It is understood that these terms are not mutually exclusive, and that a particular assay may have both attributes, as defined in this disclosure. The making and using of various embodiments of the invention is elaborated further in the sections that follow.

DEFINITIONS

The terms "confirmatory assay" and "confirmation assays", when used to describe the assays of this invention, refer to assays in which the presence of a particular analyte in a test sample is detected or confirmed, as distinguished from a potential interfering substance. For a complete reading of whether the analyte is present, both a direct and a neutralization test are performed. The direct test is an assay (typically an immunoassay) for the analyte or the interfering substance. The neutralization test is an assay (typically an immunoassay) in which the analyte has been removed or inactivated, but the interfering substance has not. Samples giving a positive reaction in the direct test but negative reaction in the confirmation test are marked as containing the true analyte. Samples giving a positive reaction in both the direct and confirmation test are marked as containing an interfering substance. Depending on context, the term "confirmatory assay" can refer to the neutralization test alone, or both tests together.

A "bidirectional antibody type confirmatory assay" is an assay in which the neutralizing antibody and the detecting antibody recognize the analyte from different orientations.

An "adsorption type confirmatory assay" is an assay in which the sample is treated with a particular amount of neutralizing antibody that is sufficient to remove the analyte but not all the interfering substance from the sample, or otherwise prevent its binding to the detecting antibody. The term "enzyme immunoassay" includes any immunoassay in which an enzyme is part of the detection system. The enzyme may be simply a tag for an active component in the reaction mixture, or it may be assembled, disassembled, activated, or deactivated in the course of the reaction. The presence of the analyte of interest in the sample may be directly or inversely correlated with enzyme activity.

The term "antibody" as used in this disclosure refers to both polyclonal and monoclonal antibodies. The ambit of the term explicitly encompasses not only intact immunoglobulin molecules, but also such fragments and derivatives of immunoglobulin molecules as may be prepared by techniques known in the art, and retaining the antibody activity of an intact immunoglobulin. Examples of antibodies other than intact immunoglobulins are provided below. In this context, "antibody activity" refers to the ability of an antibody to bind a specific antigen in preference to other potential antigens via the antigen combining site located within a variable region of an immunoglobulin.

A "detecting antibody" is an antibody that is used in an immunoassay for detecting the presence of an analyte in a sample. The detecting antibody will be able to distinguish between the analyte and other substances that may be present in the sample, although there may be a subset of substances that cross-react. The immunoassay is performed by contacting the antibody with the sample under conditions that permit the antibody to form a complex with any analyte present, and measuring any complex formed.

A "neutralizing antibody" is an antibody that is used in an assay for confirming the presence of an analyte in a sample. The neutralizing antibody will be able to bind the analyte and thereby prevent it from giving a positive reaction in an assay, particularly an immunoassay conducted with a detecting antibody.

"Cross reactivity" is determined in a quantitative immunoassay by establishing a standard curve using known dilutions of the target analyte. The standard curve is then used to calculate the apparent concentration of the interfering substance present in various known amounts in samples assayed under similar condition. The cross reactivity is the apparent concentration divided by the actual concentration multiplied by 100. The preferred immunoassay for determining cross-reactivity is a CEDIA® type assay.

An "analyte" is a substance of interest to be measured in a sample using a particular assay system. It may have any size, structure, or valence irrespective of components used in the assay system, unless otherwise specified or required. A "small molecule analyte" has a size of <5,000 mol wt and typically <1,000 mol wt.

A "substance of abuse" is a chemical not naturally occurring in the body and administered to the body in contravention of the provisions of a criminal or disciplinary code, terms of employment, terms of participation in a particular activity such as an athletic competition, or which seriously impairs an activity (such as the operation of a vehicle) to the peril of the public or those in the vicinity of the abuser, or which provides the abuser with an unfair physical or intellectual advantage in a competitive arena. Non limiting examples include canabinoids, barbiturates, amphetamines, hallucinogenic alkaloids and anabolic steroids taken for reasons other than the bona fide prevention or treatment of disease.

The term "hapten" as used in this disclosure denotes a homogeneous or heterogeneous chemical compound, generally <5,000 mol wt and typically <1.000 mol wt, with the property that a complex between the hapten and one hapten-specific antibody will inhibit the binding of a second hapten-specific antibody, regardless of whether the second antibody is different from the first or recognizes the hapten from a different orientation. In other words, a hapten has a functional valence of one with respect to antibody binding.

A "hapten derivative" denotes a compound that contains a feature of a hapten that is specifically recognizable by an anti-hapten antibody, and has been derivatized to provide it with an additional property of interest. Examples of hapten derivatives include a hapten covalently linked to a protein, and a hapten covalently linked to a solid surface (where the linkage is a covalent bond or a linking group of one or more atoms, such as may be formed by chemical synthesis or conjugation using a cross-linking agent). Other examples of hapten derivatives are haptens that have been chemically derivatized with a labeling features such as a fluorescent structure, a fluorescent quenching structure, or an enzyme inhibitor. A hapten derivative need not be functionally monovalent with respect to antibody binding—for example, a hapten-protein conjugate can optionally contain a plurality of haptens, depending on its intended role, and the valence will approach that of the conjugation ratio.

A "competitive binding compound" in the context of an immunoassay for an analyte in a sample refers to a compound which binds the detecting antibody of the immunoassay in a manner that is inhibitable by the analyte.

A substance is said to be "purified" if it is (except from solvent) at least 50%, preferably at least about 90%, and even more preferably at least 99% pure when analyzed by a suitable technique such as GC/MS. A "synthetic" compound is a compound assembled from component parts by a process that does not involve live organisms or cells.

The term "amphetamine" when used in the plural or with the indefinite article refers not only to 1-phenyl-2-aminopropane, but also 1-phenyl-2-methylaminopropane (methamphetamine), methylenedioxyamphetamine (MDA), methylenedioxymethamphetamine (MDMA), p-hydroxyamphetamine, and other structurally related sympathomimetic amines, especially phenethylamines, with psychostimulant activity.

Particular chemical structures represented in this disclosure include all stereoisomers, tautomers, salts, and protonated and deprotonated forms unless otherwise indicated.

Bidirectional Antibody Type Confirmatory Assays

A bidirectional antibody type confirmatory assay is an assay in which the neutralizing antibody and the detecting antibody recognize the analyte from different orientations. Depending on the nature of the assay, this can provide either of the following advantages:

Since the neutralizing antibody recognizes the analyte from a different direction, the chances that it will have the same cross-reactivity profile as the detecting antibody are decreased. An interfering substance with unrelated pharmacological activity that fortuitously resembles the analyte on one side is unlikely to resemble the analyte to the same extent on the opposite side.

Where desirable, neutralizing antibodies can be obtained that can be added directly to the reaction mixture without affecting the detection system. In this embodiment, no preadsorption with the neutralizing antibody is required.

The usual reagents for conducting the direct test for analyte are a detecting antibody for the analyte, and a competitive binding compound which is typically a hapten derivative. The detecting antibody binds the hapten derivative in a manner that is specifically inhibitable by the analyte. The hapten derivative is typically a modified form of the analyte or a closely related chemical structure, adapted so as to provide a signal detection system. In an assay which comprises measuring fluorescence emission or fluorescence polarization, the hapten derivative is a fluorescent hapten or a fluorescent quench hapten, typically a chemically modified form of the analyte in which the fluorescent or fluorescent quench group is adapted onto one end.

In certain types of enzyme immunoassays, the hapten derivative is a conjugate in which the hapten is linked to an enzyme, either through a covalent bond or through a bridging structure, such as may be formed using a cross-linking agent, or using a hapten chemically modified with the bridging structure with a protein-linking group on the far end. In other types of enzyme immunoassays, the hapten derivative is a conjugate in which the hapten is linked to an enzyme fragment which complements with a second enzyme fragment to form an active enzyme complex. In certain types of assays, the hapten derivative is a conjugate in which the hapten is linked to an inert substance, such as a large protein, a polymer (such as polystyrene, polyacrylamide latex, or a high molecular weight carbohydrate), a particulate, or the surface of the reaction vessel.

In any of these systems, the direct test is conducted by preparing a reaction mixture comprising the sample, the detecting antibody, and the competitive binding compound. The test is completed by measuring the amount of the complex formed between the detecting antibody and the competitive binding compound, in competition with the analyte from the sample. Depending on the detection means used, the amount of complex may correlate positively or inversely with the amount of analyte (or cross-reacting substance) in the sample.

The neutralization test is conducted in a similar fashion, using a detecting antibody for the analyte, and a competitive binding compound which is typically a hapten derivative. There is no absolute requirement that the detecting antibody, the competitive binding compound, or even the detection means be the same as in the direct test, but it is usually most convenient and most accurate if the same reagents are used in the same concentration. The neutralization test additionally involves a neutralizing antibody, which has the function of preventing a proportion of the true analyte from reacting with the detection antibody, thereby reducing the assay signal.

The neutralization test is typically conducted by preparing a reaction mixture comprising the sample, the detecting antibody, the neutralizing antibody, and the competitive binding compound or hapten derivative, and then measuring the formation of reaction complexes as in the direct test. In certain embodiments of the assay, the neutralizing antibody is preincubated with the sample in which the analyte is to be measured. Usually, however, this is not required, and it is sufficient to add the sample to a reaction mixture containing the detecting and neutralizing antibody together. In certain embodiments of the assay, the hapten conjugate reagent is added after the antibodies are in equilibrium with any analyte in the sample. More generally, the reagents may be combined in any order, depending on the kinetic parameters of the reaction system. The neutralization test is completed by measuring the amount of the complex formed between the detecting antibody and the competitive binding compound, and correlating the result with the degree of neutralization of the substance in the original sample. Successful neutralization of a sample testing positive in the direct test indicates the presence of true analyte.

Characteristics of the reagents are as follows. The hapten derivative "preferentially" binds the detecting antibody in comparison with the neutralizing antibody. This means that under assay conditions and in the absence of analyte, the proportion of hapten derivative bound to detecting antibody is at least about 10 times higher, preferably at least about 100 or 1000 times higher than that the proportion of hapten derivative bound to neutralizing antibody. Typically, the affinity of the detecting antibody for the hapten derivative is at least 10 times and preferably 100 or 1000 times higher than that of the neutralizing antibody. The affinity of the detecting antibody for the hapten derivative will generally have an affinity of at least about $10^8 M^{-1}$, with affinities of at least about $10^9 M^{-1}$, $10^{10} M^{-1}$, and $10^{11} M^{-1}$ being increasingly more preferred. The binding of the neutralizing antibody to the hapten derivative will generally have an affinity of no more than about $10^7 M^{-1}$, with affinities of no more than about $10^6 M^{-1}$ or $10^{-5} M^{-1}$ being increasingly more preferred.

Binding of the neutralizing antibody to the analyte inhibits binding of the analyte to the detecting antibody. This means that in an assay conducted in the working range in the presence of the neutralizing antibody, the binding of the analyte to the detecting antibody and subsequent specific signal generation is reduced by at least about 2-fold, and preferably 5-fold, 25-fold, or 100-fold in order of increasing preference. Higher degrees of inhibition can be obtained by using a neutralizing antibody that has a higher affinity for the analyte than does the detecting antibody. Another option is to preincubate the neutralizing antibody with the sample before adding the detecting antibody in a non-equilibrium situation. More typically, the amount of neutralizing antibody in the reaction mixture is in excess (preferably 10 fold or even 100 fold higher), thereby increasing analyte binding to the detecting antibody by mass action.

In certain embodiments of this type of assay, the neutralizing antibody also "preferentially" inhibits binding of the analyte to the detecting antibody, in comparison with a potential interfering substance. This means that in a reaction mixture containing both analyte and interfering substance within the working range of the assay, the proportion of analyte bound to the neutralizing antibody is at least about 5 times higher, preferably at least about 25, 100, or 1000 times higher than that the proportion of interfering substance bound to neutralizing antibody. Preferential inhibition may occur because the affinity of the neutralizing antibody for the analyte is at least 10 times and preferably 100 or 1000 times higher than it is for the potential interfering substance.

Any pair of detecting and neutralizing antibodies having the functional properties described in the foregoing discussion fall within the scope of the invention. Most conveniently, detecting and neutralizing antibodies are obtained by using immunogen or antibody screening or purifying reagents using different hapten-carrier conjugates, in which a chemical analog of the analyte is linked to the carrier in different orientations. The conjugate used to raise or select the detecting antibody is usually one in which the hapten is linked to the carrier in a position that is identical or nearby the position in which the hapten is linked or modified in the hapten derivative used in the assay. The conjugate used to raise or select the neutralizing antibody is selected to enhance the likelihood that the antibody will not react with the hapten derivative used in the assay, in accordance with the properties described above. Thus, the conjugate presents the hapten so as to elicit antibodies that will be sterically inhibited from reacting with the hapten derivative of the assay (in the case of an enzyme conjugate), or will be faced with the signaling moiety of the hapten derivative (in the case of a fluorescently modified analog) and be unlikely to cross-react. Typically, but not necessarily, the presentation of the hapten used to raise the detecting and neutralizing antibodies will be from opposite ends of the molecule.

The nature of the reagents and the means of obtaining them will be further appreciated by way of the illustrations provided later in this section, and in the examples.

Exemplary confirmatory assays are based on the CEDIA® DAU immunoassay technology. The assay method is a homogeneous enzyme complementation assay, in which enzyme donor and enzyme acceptor fragments of β-galactosidase combine to form an active enzyme complex. The enzyme donor is conjugated with an analog of the test analyte, and a reagent antibody against the analyte is also present in the reaction mixture. When no analyte is present, the antibody binds to the enzyme donor conjugate, which is thereby inhibited from complementing the enzyme acceptor to form an active enzyme. When test analyte is present, it binds the antibody, the antibody cannot bind the enzyme donor, and enzyme complementation occurs. Thus, the rate of enzyme catalysis (measured by conversion of a chromogenic substrate) is directly related to the amount of analyte in a test sample.

One particular example is based on the CEDIA® DAU immunoassay for LSD. The detecting antibody in the kit was raised to LSD attached at the indole nitrogen to the immunogenic carrier protein KLH via a linker arm. Structure "A" (below) shows an activated LSD derivative used to prepare the immunogen, in which LSD) is linked to KLH through the indole ring; specifically at the N–1 position. (Antibodies can also be raised using KLH conjugates formed by the Mannich reaction, in which LSD is linked through the 2 position.) The enzyme donor in the kit is a conjugate in which the LSD is linked to the β-galactosidase through the same N–1 position. Neutralizing antibodies suitable for use in a confirmation assay can be obtained using an immunogen generated using structure "B", in which LSD) is linked to the carrier protein via the alkyl amide group.

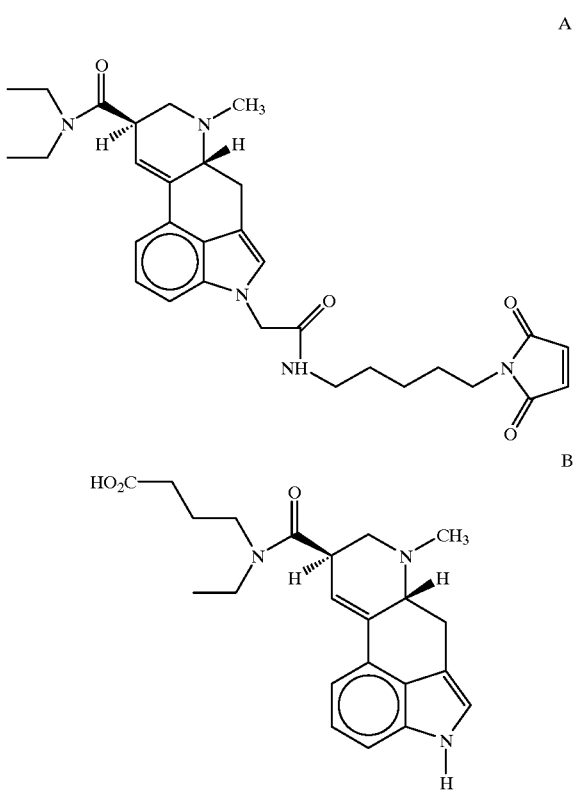

Another example is based on the CEDIA® DAU immunoassay for amphetamines. This kit measures both 1-phenyl-2-aminopropane (amphetamine) and 1-phenyl-2-methylamimorpropane (methamphetamine), using separate detecting antibody-enzyme donor reagent pairs in the same reaction mixture. The two detecting antibodies were raised to amphetamine and metlhamplhetamine attached to carrier proteins via the phenyl ring. Structure "C" (below) shows the chemistry of activated amphetamine derivative used to prepare the immunogen (where R=H for amphetamine and R=$CH_3$ for methamphetamine). Neutralizing antibodies suitable for use in a confirmation assay can be obtained using an immunogen generated using structure "D", in which an amphetamine is linked to the carrier protein via the alkyl amide group. A neutralizing antibody can be selected that commonly removes both amphetamine and methamphetamine, or separate antibodies can be obtained each of which removes one of the two compounds.

C

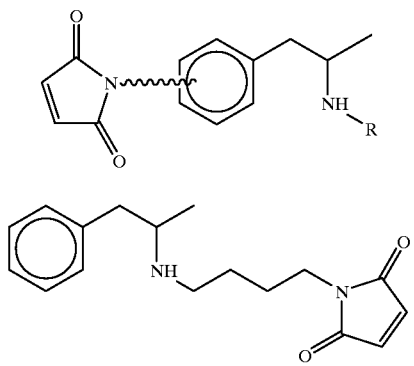

D

Details for synthesis of these compounds are provided in the example section.

In a similar fashion, neutralizing antibodies can be obtained that are suitable with other established detection assays for small molecule drugs. For example, for amphetamine assays based on the glucose-6-phosphatic dehydrogenase homogeneous assay system, a neutralizing antibody is obtained using conjugates of Structure C or Structure D, above, selected to present the amphetamine in an opposite direction from that of the G6PD conjugate. For amphetamine assays in which amphetamine is linked to a solid surface via the phenyl ring, the neutralizing antibody will be raised or selected using conjugates in which an amphetamine is linked to the carrier protein via the alkyl amine group, and vice versa. For amphetamine assays using, fluorescent tracers of the nature described in U.S. Pat. No. 4,952,336 (phenethylamines with a fluorescent group attached to the p-position), antibodies raised using conjugates in which an amphetamine is linked to the carrier protein via the alkyl amine group are likely to be the most effective neutralizers. For amphetamine assays using fluorescent tracers of the nature described in E.P. Patent 371, 253-B (phenethylamines with a fluorescent group attached to the alkyl amine (group), antibodies raised using conjugates in which an amphetamine is linked to the carrier protein via the phenyl ring are likely to be the most effective neutralizers.

Antibody pairs for use in bidirectional type confirmatory assays for PCP (phencyclidine; 1-(1-phenylcyclohexyl) piperidine)) can be prepared using PCP immunogens according to Structure E and Structure F, shown below. PCP chemistry and assays are described in Ceneste et al. (Bull. Soc. Chim. France 11:610. 1978) and Katz et al. (Theriogenology 6:2–3, 1976).

E

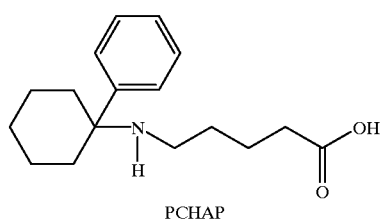

PCHAP

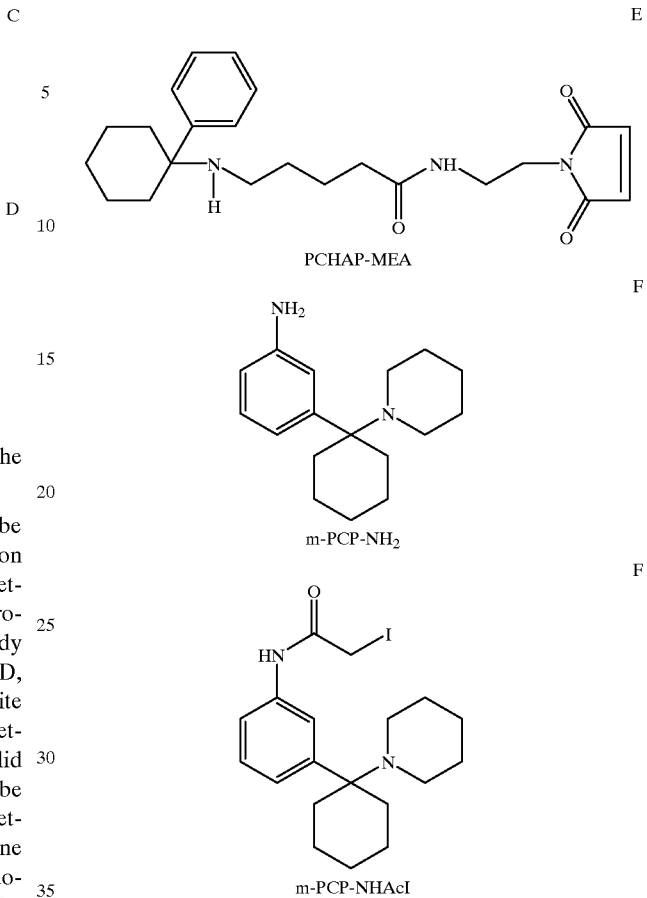

PCHAP-MEA m-PCP-NH₂ m-PCP-NHAcI

To use the antibodies raised against Structures E and F as the detecting and neutralizing antibody, respectively, the hapten conjugate is prepared according to Structure E. To use the antibodies raised against Structures F and E as the detecting and neutralizing antibody, respectively, the hapten conjugate is prepared according to Structure F.

Adsorption Type Confirmatory Assays

In an adsorption-type confirmation assay, the sample is treated with a particular amount of neutralizing antibody that is sufficient to remove the analyte but not all of a particular interfering substance from the sample, or otherwise prevent its binding to the detecting antibody.

The neutralizing antibody preferentially binds the analyte in comparison with the interfering substance, meaning that it binds the analyte about 5 times better, preferably at least about 25, 100, or even about 1000 times better, compared with potential interfering substance. Preferential inhibition may occur because the affinity of the neutralizing antibody for the analyte is at least 10 times and preferably 100 or 1000 times higher than it is for the potential interfering substance.

The neutralizing antibody can optionally be different from the detecting antibody. However, it has been discovered that this is not critical to the practice of adsorption type confirmatory assay in a number of its embodiments. The assay can be performed by using the same antibody for both neutralizing and detecting. The key is to provide enough antibody at the neutralizing step to remove or inactivate the analyte, but not enough to remove or inactivate the interfering material. The technique takes advantage of the following two features: first, the specificity of the antibody, as indicated in the preceding, paragraph; and second, the fact that the interfering substance must be present in large molar excess in order to have given a positive reaction in the direct test.

A simple hypothetical example will illustrate the point. Suppose the antibody used to detect the analyte has a high affinity for analyte, and cross-reactivity for the interfering substance of 1%. When the interfering substance is present at 1000 nM, it will give about the same signal in the direct test as analyte at 10 nM. Now, take the same antibody and use it to pre-adsorb the sample, but provide only sufficient antibody to adsorb 50 nM. At equilibrium. the antibody should adsorb nearly all the analyte in a 10 nM sample, but no more than about 5% of the interfering substance in a 1000 nM sample (probably less, since the affinity for interfering substance is lower). Thus, the true analyte will give a negative result in the neutralization test, but the interfering substance will give a positive result.

One of skill in the art will appreciate that it is not necessary for the neutralizing antibody to remove or inactivate absolutely all of the analyte, providing that it removes a greater proportion of analyte than interfering substance. In this way, thresholds can be set in the confirmatory part of the test that can be recorded as negative (confirming the presence of analyte) or positive (indicating the presence of interfering substance).

The neutralizing antibody can act to prevent the analyte from reacting with the detecting antibody in the detection phase of the confirmatory test by several different mechanisms. In one mechanism, the neutralizing antibody simply binds the analyte at the same epitope (in a similar or dissimilar orientation) as the detecting antibody. Since the neutralizing antibody should not then go on to substitute for the detecting antibody, the detection means must involve some difference between the two. In one example, the detecting antibody is conjugated to the labeling system, such as in the enzyme complementation assay described in U.S. Pat. No. 5,212,064. The neutralizing antibody could be the same Fab fragment (or the whole antibody equivalent) in an unconjugated form, and would prevent binding to the detection conjugate. In another example, the neutralizing antibody recognizes the analyte from a different orientation from the detecting antibody and is unable to react with the detection system in the same way.

More typically, the neutralizing antibody is used to pretreat the sample and remove the true analyte in preference to the interfering substance. Then the sample is tested using a detection antibody and competitive binding compound in a similar fashion to the direct test. Any type of immunoadsorption can be used. Typically, the neutralizing antibody is "insolubilized", which means that it is attached to an insoluble polymer or bead made of a suitable inert material, such as polystyrene, polyacrylamide, cellulose, and the like, or the side of a vessel wall through which the sample is passed or preincubated. An affinity separation step can be performed by column chromatography or filtration. However, elaborate separation procedures are generally not necessary. A convenient procedure is to simply add an affinity matrix into the sample, keep in suspension for sufficient time to adsorb the analyte, and then allow it to settle to the bottom of the reaction vessel. The supernatant can then be assayed for interfering substance.

In a variation of this approach the neutralizing antibody is not attached directly to a solid surface, but insolubilized after it is added to the sample. A secondary capture antibody or binding compound can be used for this purpose. For example, if the neutralizing antibody is a mouse anti-analyte antibody, then the capture antibody can be a polyclonal rabbit anti-mouse immunoglobulin reagent bound to a solid phase. In another example, the neutralizing antibody can be provided with a suitable capture ligand, such as fluorescein or biotin. Following incubation with the sample, the antibody (along with bound analyte) is removed using a receptor with the matching specificity: respectively anti-fluorescein antibody, or avidin. In a further variation of this approach., the primary antibody or the capture antibody is linked to a ferromagnetic particle, which is subsequently removed from the solution (along) with the analyte) using a magnetic field.

Whatever the mechanism for removing or inactivating the true analyte, the amount of neutralizing antibody is adjusted so as to be sufficient to remove the analyte but not all the interfering substance. Where the neutralizing antibody is linked to a particulate, it can be diluted as needed by adding additional particulate which has not been activated or which is linked to an alternative, inactive molecule such as bovine albumin. This permits an appropriate amount of antibody to be provided in an easily handled amount of particulate. This is illustrated in Example 6.

An assay for distinguishing between the analyte and an interfering substance involves conducting an immunoassay to determine the amount of analyte and/or interfering substance in the sample (the direct test); treating the same sample or a duplicate of the sample with a neutralizing antibody in an amount sufficient to remove or inactivate the analyte but not the potential interfering substance; and conducting an immunoassay to determine the amount of interfering substance in the treated sample (the confirmatory test). The direct and confirmatory immunoassays are performed by preparing a reaction mixture comprising the sample, a detecting antibody, and a competitive binding, compound (usually a hapten derivative), wherein the detecting antibody binds the hapten derivative in a manner that is specifically inhibitable by the analyte and then measuring the amount of the detecting antibody bound to the hapten derivative. As before, there is no absolute requirement that the detecting antibody, the hapten derivative, and the detection means be the same for the two tests, but this is generally more convenient.

Exemplary are adsorption type confirmatory assays for amphetamine and LSD, using a neutralizing antibody insolubilized by attaching directly to a resin such as Sepharose® 4B. Example 7 provides an illustration of an adsorption-type confirmatory test for LSD, in which the detecting antibody and the neutralizing antibody are the same. The commercially available CEDIA DAU® kit contains a detecting antibody raised by linking the following activated LSD derivative to KLH, and an enzyme donor made with the same derivative:

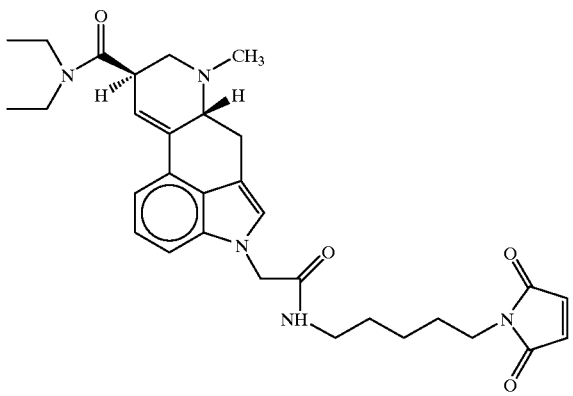

The detecting antibody has the laboratory designation 19A7. Example 6 illustrates the preparation of an insolubilized form of 19A7 and adjustment of the activity to provide a suitable neutralizing reagent for a confirmatory assay. The assay is illustrated in Example 7. In a panel of 32 clinically obtained samples, the assay correctly identified the 27 samples that contained LSD, and five samples that were false positive, as verified by GC/MS. Confirmatory assays preferably have a success rate of at least 75% and more preferably at least about 95% in identifying false positives due to interfering substances, within the standard working range of the assay.

Assay Reagents and Kits

Taking into account the principles described in the preceding sections, the preparation of detecting and neutralizing antibodies for use in this invention is performed according to established techniques, using an immunogen that presents the hapten in an appropriate orientation. The hapten is typically a structure that is identical or closely related to the analyte to be measured, linked to an immunogenic carrier such as KLH either directly or through a linking group.

For general techniques used in raising, purifying and modifying antibodies, and the design and execution of immunoassays, the reader is referred to *Handbook of Experimental Immunology* (D. M. Weir & C. C. Blackwell, eds.); *Current Protocols in Immunology* (J. E. Coligan et al., eds., 1991); David Wild, ed., *The Immunoassay Handbook* (Stockton Press New York, 1994); and R. Masseyeff, W. H. Albert, and N. A. Staines, eds., *Methods of Immunological Analysis* (Weinheim: VCH Verlags gesellschaft mbH, 1993).

Polyclonal antibodies of this invention are raised by administration of the immunogenic conjugate to a mammalian host, usually mixed with an adjuvant. The immunogen is conveniently prepared for injection by rehydrating lyophilized immunogen to form a solution or suspension. Preferred adjuvants are water-in-oil immersions, particularly Freund's complete adjuvant for the first administration, and Freund's incomplete adjuvant for booster doses. The preparation is typically administered in a variety of sites, and typically in two or more doses over a course of at least 4 weeks. Serum is harvested and tested for the presence of specific antibody using a hapten-protein conjugate or other competitive binding compound for the analyte in a standard immunoassay or precipitation reaction.

Polyclonal antisera will typically contain antibodies not reactive with the analyte or having undesired cross-reactivities. Methods for purifying specific antibodies from a polyclonal antiserum are known, particularly affinity purification using a column of analyte conjugated to a solid phase. The antiserum is passed over the column, the, column is washed, and the antibody is eluted with a mild denaturing buffer such as 0.1 M glycine, 0.2 M NaCl, pH 2.5. If the antiserum is passed over the column in a buffer containing potential interfering substances, then the bound and eluted fraction will be enriched for antibodies that don't cross-react.

Monoclonal antibodies of this invention can be prepared by a number of different techniques known in the art. For hybridoma technology, the reader is referred generally to Harrow & Lane (1988), U.S. Pat. Nos. 4,491,632, 4,472, 500, and 4,444,887, and *Methods in Enzymology*, 73B:3 (1981). The most common way to produce monoclonal antibodies is to immortalize and clone a splenocyte or other antibody-producing cell recovered from an immunized animal. The clone is immortalized by a procedure such as fusion with a non-producing myeloma, by transfecting with Epstein Barr Virus, or transforming with oncogenic DNA. The treated cells are cloned and cultured, and clones are selected that produce antibody of the desired specificity. Specificity testing is performed on culture supernatants by a number of techniques, such as using the immunizing antigen as the detecting reagent in an immunoassay. A supply of monoclonal antibody from the selected clone can then be purified from a large volume of culture supernatant, or from the ascites fluid of suitably prepared host animals injected with the clone. The antibody can be tested for activity as raw supernatant or ascites, and is optionally purified using standard biochemical preparation techniques such as ammonium sulfate precipitation. ion exchange chromatography, and gel filtration chromatography.

Alternative methods for obtaining monoclonal antibodies involve contacting an immunocompetent cell or viral particle with a the desired analyte or an analyte-protein complex in vitro. In this context, "immunocompetent" means that the cell or particle is capable of expressing an antibody specific for the antigen without further genetic rearrangement, and can be selected from a cell mixture by presentation of the antigen. Immunocompetent eukaryotic cells can be harvested from an immunized mammalian donor, or they can be harvested from an unimmunized donor and prestimulated in vitro by culturing in the presence of immunogen and immunostimulatory growth factors. Cells of the desired specificity can be selected by contacting with the immunogen under culture conditions that result in proliferation of specific clones but not non-specific clones. Immunocompetent phage can be constructed to express immunoglobulin variable region segments on their surface. See Marks et al., New Engl. J. Med. 335:730, 1996: WO patent applications 94/13804, 92/01047, 90/02809; and McGuinness et al., Nature Biotechnol. 14:1149, 1996. Phage of the desired specificity can be selected, for example, by adherence to a hapten-protein complex attached to a solid phase, and then amplified in *E. coli*.

The term "antibody" as used in this disclosure encompasses not only intact immunoglobulin molecules, but also such fragments and derivatives (including recombinant derivatives) of immunoglobulin molecules with the desired specificity. Fragments and other derivatives of immunoglobulins can be prepared by methods of standard protein chemistry, such as subjecting the antibody to cleavage with a proteolytic enzyme like pepsin, papain, or trypsin; and reducing disulfide bonds with such reagents as dithiothreitol. Genetically engineered variants of intact immunoglobulin can be produced by obtaining a polynucleotide encoding the antibody, and applying the general methods of molecular biology to splice encoding sequences or introduce mutations and translate the variant. Antibodies that are engineered variants of particular interest include chimeric and humanized antibodies, Fab-like fragments, single-chain variable region fragments (scFv), and diabodies.

Detecting antibodies for use in enzyme complementation assays in the CEDIA® series are selected on the basis of specificity for the analyte, and also on the basis of three other criteria. One, referred to as "inhibition", relates to how well the antibody binds the enzyme-donor conjugate. Sufficient inhibition (preferably at least about 70%) is needed in order to provide an adequate signal. A second criterion is the titer of the antibody required to obtain the desired level of inhibition. Inhibition at lower antibody levels is preferred. A third criterion, referred to as "modulation", relates to how well the sample analyte is able to compete with the conjugate for enzyme binding. Modulation is calculated as the difference in enzyme rate between a sample having the analyte at a target concentration (moderately chosen within the intended working range) and a sample having no analyte, divided by the rate at the target concentration. Better modulation correlates with better assay sensitivity. Detecting antibodies for other types of assays are selected by criteria appropriate to provide the desired sensitivity and specificity through the working range.

Neutralizing antibodies are selected on the basis of criteria necessary for their use in the intended assay system. Neutralizing antibodies that are maintained in the reaction mixture during the detection of any uncomplexed interfering substance, such as in a bidirectional type confirmatory assay, must not react with the other reagents in the mixture and give a false signal. In particular, they must not be able to take the place of detecting antibody in binding to any hapten derivative involved in signal generation. Thus, neutralizing antibodies are selected that don't have this activity, either by direct negative selection for the unwanted binding characteristic, or by negative selection in an assay mixture according to the immunoassay method in the absence of detecting antibody.

Antibodies can be "insolubilized" by attaching them to a vessel wall, to a particulate, or to a large molecular weight carrier that can be kept in suspension but is removable by physicochemical means, such as centrifugation or microfiltration. The attachment need not be covalent, but is at least of sufficient permanence to withstand any separation techniques (including washes) that are part of the assay procedure. Suitable particulate materials include agarose, polystyrene, cellulose, polyacrylamide, latex particles, magnetic particles, and fixed red cells. Suitable commercially available matrices include Sepharose® (Pharmacia), Poros® resins (Boehringer Mannheim Biochemicals, Indianapolis), Actigel Superflow™ resins (Sterogene Bioseparations Inc., Carlsbad Calif.), and Dynabeads™ (Dynal Inc., Lake Success, N.Y.). The choice is not critical, and will generally depend on such features as stability, capacity, accessibility of the coupled antibody, flow rate (or the ability to disperse the resin in the reaction mixture), and ease of separation.

Suitable approaches for attaching the antibody to the resin are shown in the following table:

TABLE 1

Conjugation Chemistry

| Site of Attachment or Derivitization on Resin | Reagent Used | Site of Attachment of Antibody |
| --- | --- | --- |
| Hydroxyl groups | CNBr | Amino groups |
| Hydroxyl groups | Carbonyldiimadazole | Amino groups |
| Aldehyde groups | $NaBH_4$ or $NaCNBH_3$ | Amino groups |
| Sulfhydryl-reactive group ($RCH_2I$, R-maleimide, disulfide) | (Spontaneous) | Disulfide bonds (after reduction) |
| Amino groups | Water-soluble carbodiimides | Carboxyl groups |
| Carboxyl groups | Water-soluble carbodiimides | Amino groups |
| N-hydroxysuccinimide esters | (Spontaneous) | Amino groups |
| Epoxide groups | (Spontaneous) | Amino groups |
| Hydrazide groups | (Spontaneous) | Carbohydrate groups (after periodate oxidation) |
| Protein A or Protein G | (Spontaneous) | Antibody Fc region |

Competitive binding compounds and hapten derivatives for use in the invention are prepared according to the chemistry of the analyte to be measured, and the detection system in the selected assay system.

This invention includes various sets of reagents, which are effective in performing a confirmatory assay of this invention, or in adapting a direct assay for distinguishing between an analyte and an interfering substance. For sets that include a plurality of reagents, it is not necessary that the reagents all be sold together or by the same distributor, so long as they have the desired functionality. It may be appropriate to distribute the reagents separately, for example, when the shelf life of one reagent is shorter than that of the rest of the system.

This invention also includes kits, in which one or more reagents are provided in suitable packaging. The reagents are optionally aliquoted so that they can be readily used in a clinical system. A kit will often contain written instructions for the performance of a confirmatory assay. This can be limited to a simple indication on the packaging that the ingredients are suitable for confirmatory tests, eliminating false positives, or distinguishing the analyte from named or unnamed interfering substances. Preferably, the written instructions will also indicate important steps and conditions for performing the tests, and data useful in interpreting the tests. For adsorption type confirmatory assays, the kit preferably contains an indication of the amount of neutralizing antibody to be added to each sample, or the neutralizing antibody will be pre-aliquoted in the appropriate amount.

Assay Procedure

The assay procedure entails combining the sample with the antibody under conditions that permit the formation of a stable complex between the substance to be tested and the antibody. This is followed by detecting any antigen-antibody complex that is formed. A "stable complex" is a complex that persists at least as long as it takes the presence of the complex to be measured by the intended method.

Assays suitable for use or modification in this invention include both qualitative and quantitative assays. Typical quantitative methods involve mixing the analyte with a pre-determined non-limiting amount of the reagent antibody, and correlating the amount of complex formed with the amount of analyte in the original sample using a relationship determined using standard samples containing known amounts of analyte in the range expected for the sample to be tested. In a qualitative assay, sufficient complex above or below a threshold level established by samples known to contain or be free of analyte establish the assay result. Unless otherwise required, "measuring" refers both to qualitative and quantitative determination.

Assays of this invention include both separation-based and homogeneous assays. In separation based assays, the detecting of the complex involves a process wherein the complex formed is physically separated from either unreacted analyte, unreacted antibody, or both. See, e.g., U.S. Pat. No. 3,646,346. The complex can be first formed in the fluid phase, and then subsequently captured by a solid phase reagent or separated on the basis of an altered physical or chemical property, such as by gel filtration or precipitation. Alternatively, one of the reagents can be attached to a solid phase before contacting with other reagents, and then the complex can be recovered by washing the solid phase free of unreacted reagents. Separation-based assays typically involve use of a labeled analog or antibody to facilitate detection or quantitation of the complex. Suitable labels are radioisotopes such as $^{125}$I, enzymes such as peroxidase and β-galactosidase, and fluorescent labels such as fluorescein isothiocyanate. The separation step involves removing labeled reagent present in complex form from unreacted labeled reagent. The amount of label in the complex can be measured directly or inferred from the amount left unreacted. By way of example, a sample can be tested for amphetamine by mixing with labeled anti-amphetamine antibody and solid-phase amphetamine. After washing, the amount of label bound to the solid phase inversely correlates with the amount of amphetamine in the sample.

In homogeneous assays, the complex is typically not separated from unreacted reaction components, but instead the presence of the complex is detected by a property which at least one of the reactants acquires or loses as a result of being incorporated into the complex. Homogeneous assays known in the art include systems involving fluorochrome and fluorochrome quenching pairs on different reagents (U.S. Pat. Nos. 3,996,345, 4,161,515, 4,256,8344 and 4,261,968); enzyme and enzyme inhibitor pairs on different reagents (U.S. Pat. Nos. 4,208,479 and 4,233,401); and chromophore and chromophore modifier pairs on different reagents (U.S. Pat. No. 4,208,479).

Assays of this invention include both sandwich and competition assays. Sandwich assays typically involve forming a complex in which the analyte to be measured is sandwiched between one reagent, such as a first antibody used ultimately for separation of the complex, and another reagent, such as a second antibody used as a marker for the separated complex. For small molecule drugs, competition assays are more common. Competition assays involve a system in which the analyte to be measured competes with an analog of the analyte for binding to another reagent, such as an antibody. In the context of immunoassay, a "competitive binding compound" refers to a compound that is able to compete with the analyte to be measured in the sample for binding to the detecting antibody. Competitive binding compounds are identified functionally, and include radioisotope conjugates, enzyme conjugates, and other protein complexes, and structurally similar chemical analogs. CEDIA® is an example of a competition assay.

Homogeneous assay methods of this invention are exemplified by enzyme complementation assays, exemplified by the cloned enzyme donor immunoassay system described in U.S. Pat. No. 4,708,929. Related reagents and methods are taught in U.S. Pat. Nos. 5,254,577; 5,444,161; 5,464,747; and 5,514,560. Cloned enzyme donor immunoassays are available commercially under the registered trademark CEDIA®. Typically, a cloned enzyme donor immunoassay involves combining the sample with a specific detecting antibody; an enzyme donor polypeptide conjugate; an enzyme acceptor polypeptide (wherein the enzyme acceptor polypeptide is capable of forming with said enzyme donor polypeptide conjugate an active enzyme complex in the absence of an antibody to the analyte), and a substrate capable of being transformed by the active enzyme complex into a product. The amount of product is then measured, usually as a function of time.

Preferred enzyme-donor and enzyme-acceptor polypeptides are based on the enzyme β-galactosidase polypeptide. A "β-galactosidase polypeptide" is a polypeptide identifiable on the basis of its amino acid sequence or enzymatic activity as being developed from an enzyme with β-galactosidase activity, and includes naturally occurring β-galactosidase, fragments, deletion mutants, fusion proteins, mutants, and other variants. Particular β-galactosidase polypeptides are described in the aforelisted U.S. Patent applications pertaining to cloned enzyme donor immunoassays.

β-galactosidase enzyme acceptors are preferably produced by a deletion mutant of the β-galactosidase gene. EA 22, one of the preferred acceptors, has a deletion of amino acid residues 13–40. Other enzyme acceptor fragments of β-galactosidase include EA5, EA11, EA14, EA17, EA18, EA20, EA23 and EA24. The distal end of the deleted segment normally falls between amino acid positions 26 and 54 of the β-galactosidase sequence. In EA22, the distal end of the deletion segment is amino acid 40.

A particularly preferred β-galactosidase enzyme donor is ED28. This is a fragment of β-galactosidase consisting of amino acids 1–46, with cystic residues at positions 1 and 46. ED28 is described in European Patent Application No. 90308937.3. The two cysteine residues can be used for exact and reproducible placement of maleimide adducts of a chemical hapten, as illustrated in the examples.

Preferred substrates for use in immunoassays based on P-galactosidase include those described in U.S. Pat. Nos. 5,032,503: 5,254,677; 5.444,161 and 5,514,560, Amongst the preferred substrates is chlorophenol β-D-red galactopyranoside (CPRG).

CEDIA® type homogeneous assays for small molecule analytes are often formulated such that an analog of the analyte is attached to the enzyme donor near a site involved in recombination of the donor and acceptor. For example, assays for procainamide and N-acetylprocainamide (NAPA) are described in (U.S. Pat. Nos. 5,439,798 and 5,525,474. Binding of an antibody in the solution to the analog, in the conjugate inhibits recombination into an active enzyme complex. Thus, the presence of analyte in the sample is positively correlated with enzyme activity. U.S. Pat. No. 5,212,064 describes a different approach, in which the antibody fragment is conjugated to the enzyme donor, and the analog is conjugated to a macromolecule or insoluble particle. Binding of the enzyme donor to the analog conjugate via the antibody sterically inhibits recombination with the enzyme acceptor. Analyte in the sample competes with the analog conjugate, freeing up the enzyme donor for recombination with the acceptor. Again, the presence of analyte in the sample is positively correlated with enzyme activity.

Other assay systems of particular interest are enzyme immunoassays based on glucose-6-phosphate dehydrogenase (G6PD). Examples are provided in International Patent Application WO 94/24559 and EP Patent Application 487, 301-A. A homogeneous assay can be performed, in which G6PD is conjugated with an analog of the analyte in a position where binding of an antibody to the analog inhibits G6PD activity. If the test sample contains the analyte of interest, it competitively binds the antibody, which is then prevented from binding the G6PD. Thus, enzymatic activity correlates positively with the presence of analyte in the sample. The assays in the Behring Emits® II series, including the amphetamine/methamphetamine assay, are homogeneous assays using G6PD) conjugates, in which absorbance change of NAD to NADH is measured spectrophotometrically. Assays in this series can be converted for confirmation testing by supplying a neutralizing antibody according to this invention.

Other assay systems of particular interest are fluorescence polarization immunoassays. Reagents, methods and kits for an amphetamine-class fluorescence polarization immunoassay is provided in U.S. Pat. No. 5,354,693 and E.P. Patent 371,253-B. The binding of antibody to the fluorescent amphetamine derivative affects the fluorescence polarization signal. Competition with an amphetamine in the test sample proportionally affects the signal, which can be quantified in terms of millipolarization units and correlated with amphetamine concentration. The Amphetamine/Methamphetaminie II assay in the TDx®/TDxFLx® series of Abbott Laboratories is an example of a fluorescence polarization assay. The assays can be converted for confirmation testing by supplying a neutralizing antibody according to the invention. Amphetamine analogs shown in U.S. Pat. No. 5,354,693 and E.P. Patent 371,253-B differ in the position at which the fluorescent group is attached, and may require different neutralizing antibodies for use in a bidirectional type assay, as described earlier.

The assay methods of this invention can be carried out manually, or on automated equipment. Devices suitable for confirmatory assays generating an enzymatic signal include analyzers in the Beckman Synchron™ series, Olympus analyzers (AU800, AU5000, AU 5200), Roche COBAS® analyzers, and devices in the Boehringer Mannheim/Hitachi series. Analyzers suitable for performing bidirectional antibody type confirmation assays for amphetamine, similar to those illustrated in Example 4, include BM/Hitachi models 704, 717, 747, 902, 904, 911, 912, 914, and 917. Analyzers suitable for performing adsorption type confirmation assays for LSD, similar to those illustrated in Example 7, include BM/Hitachi models 902, 911, 912, and 717. The experiments described in Example 4 and Example 7 were performed primarily using a BM/Hitachi model 911 automated analyzer.

Use of Confirmatory Assays

As indicated elsewhere in this disclosure, the full detection and confirmation of the analyte involves two tests: a) a direct test for any analyte or interfering substance in the sample, and b) a neutralization or confirmation test, in which the analyte (but not interfering substances) is removed or prevented from generating a signal by treating with a neutralizing antibody. The actual sample used in step b) may be the same sample aliquot used in step a), but is more typically a duplicate sample aliquot, preferably subdivided or siphoned from the same sample aliquoted for step a).

Interpretation of the results is as follows: If the amount measured in step a) is below the threshold of detectability for the test, then the absence of analyte or any interfering substance is determined at the corresponding level of sensitivity. If the amount measured in test a) is significantly different from the amount measured in test b), then the presence of the true analyte (or an indistinguishable analog) is determined. If the amounts measured in the two tests are not significantly different, then the absence of detectable analyte is determined. Depending on its reactivity, the neutralizing antibody may remove a proportion of the interfering substance. Thus, the threshold beyond which the direct and neutralizing tests are "significantly different" is the level at which the difference can no longer be attributed to reaction with interfering substance alone. The threshold can be determined empirically by testing a range of samples spiked with various levels of analyte and potential interfering substances, or by testing a panel of clinical samples confirmed by GC/MS. For illustration, see Examples 4 and 7.

Since immunoassay embodiments of this invention are used frequently as screening assays, it is worthwhile to get further independent confirmation of a result that indicates presence of a true analyte, especially where there are substantial consequences of a positive result. For small molecules, the techniques of GC/MS, LC/MS, GC/MS/MS or LC/MS/MS are generally preferred, and certain combinations of liquid chromatography are also suitable where the results are definitive.

Situations arise in which both the direct and the confirmation parts of the assay will be positive when the true analyte is present. The most common situation is when the analyte is present at such high concentration in the solution that it exceeds the functional capacity of the neutralizing antibody. This is readily recognized by the extent of the reaction in the direct test. It is prudent to set an upper limit for the assay that is below this capacity as determined empirically. Beyond the limit, samples should be diluted and retested, or more preferably, subjected to an independent analysis such as GC/MS. By way of illustration, it is recommended that samples testing over 8,000 ng/ml in the amphetamine assay described in Example 4 be analyzed by GC/MS, regardless of the result of the confirmation part of the immunoassay.

The other situation where both the direct and confirmation part of the assay could give a positive result is when both the true analyte and the interfering substance are present in the sample. Particularly when the amount of interfering substance is high, it will be difficult to observe the effect of the neutralizing antibody on any true analyte present in the same sample. Caution is advised against excluding samples from GC/MS analysis when the results of the confirmatory assay are high, and there is reason to suspect fortuitous or deliberate masking by the administration of an interfering drug.

Quantitation in a confirmatory assay of this invention and the ability to distinguish the analyte from the interfering substance can optionally be enhanced by measuring relative rate of enzyme catalyzed conversion of the substrate to a product between the reaction mixture for the direct test and the reaction mixture for the confirmatory test. This is illustrated in Example 7. The rate of reaction in the two tests can be measured simultaneously or sequentially. Calculation of the differential rate facilitated in automated devices equipped for this purpose, such as the BM/Hitachi analyzer model 911. Procedures for performing a calculated test (in which results of multiple channels are used to calculate a final result using a pre-programmed equation) will be described in the technical manual for the device.

The products and methods of this invention can be applied for the determination or measurement of any analyte of interest, wherever a suitable primary detecting assay exists, and a neutralizing antibody that meets the requirements of the invention can be obtained. Such analytes include synthetic chemical structures including but not limited to pharmaceutical compounds, peptides, carbohydrates, lipids, environmental agents and contaminants. Pharmaceutical compounds of various kinds can be measured, for example, to monitor the pharmacological profile of a prescribed drug, to determine excretion rates in renal function tests, or to ascertain drug abuse.

The measuring, of substances of abuse is exemplary. In certain embodiments of the invention, drugs of abuse and their metabolites are both considered positive, and are distinguished from unrelated cross-reactive interfering substances. In other embodiments, the drugs of abuse are distinguished from their metabolites (see Example 7). Particular abused substances of interest are those identified in the National Institute of Drug Abuse (NIDA) guidelines, which also provides cut-off levels for drug screening.

The following compounds are potentially interfering due to unexpected cross-reactivities and the possibility that they may be present in high concentrations, particularly in urine samples: acetaminophen, ASA, amitriptylene, amoxicillin, amphetamine, ascorbic acid, atrophine, benzoylecgonine, caffeine, captopril, chlordiazepoxide, chloroquine, cimetidine, codeine, dopamine, diazepam, digoxin, enalapril, erythromycin, estriol, fluoxetine, ibuprofen, levothyroxine (T4), methamphetamine, morphine, naproxin, nifedipine, phencyclidine, phenobarbital, ranitidine, salicyluric acid, secobarbital, tolmetin, verapamil and tetrahydrocanabinol and its derivatives. Potentially interfering substances in LSD assays include methamphetamine, fenfluramine, ambroxol, chlorpromazine, ergotryptine, dihydroergotamine, ecogonine and related compounds, ergonivine, ergotamine, lysergic acid, lysergol, methysergide maleate, psilocybin, psilocyn, seretonine, tryptophan, fentanyl, and 2-oxo-3-hydroxy LSD. Potentially interfering substances in PCP assays include dextramethorphan and EDDP. Potentially interfering substances in opiate assays include imipramine, rifampicin, ofloxin, meltrexone, and naloxone. Potentially interfering substances in benzodiazepine assays include non-steroidal anti-inflammatory drugs such as oxyprozin. Potentially interfering substances in methadone assays include EDDP, EMDP, and disopyramide. Potentially interfering substances in amphetamine assays include ephedrine, pseudoephedrine, phenylpropanolamine, phentermine, fenfluramine, 3-hydroxytyramine, norpseudoephedrine, mephentermine, and phendimetrazin.

Samples that can be tested using the products and methods of this invention are by no means limited to urine samples. Where the analyte is a substance that has been administered to a human or animal subject, or a metabolite of an administered substance, suitable samples include serum, plasma, and other blood fractions; spinal fluid, sinovial fluid, and saliva. Suitable samples also include tissue culture supernatants, tissue homogenates, plant products, and other types of laboratory concoctions. Suitable environmental samples for testing include any aqueous sample with a detectable analyte for which it is desirable to distinguish from an interfering substance against which a neutralizing antibody can be obtained.

Illustration of the development and use of reagents and assays according to this invention are provided in the Example section below. The examples are provided as a further guide to a practitioner of ordinary skill in the art, and are not meant to be limiting in any way.

EXAMPLES

Example 1

Detecting Antibodies and Assays for Amphetamine and Methamphetamine

Amphetamine protein conjugates were prepared by using an activated amphetamine derivative of the following structure (BMP-amphetamine):

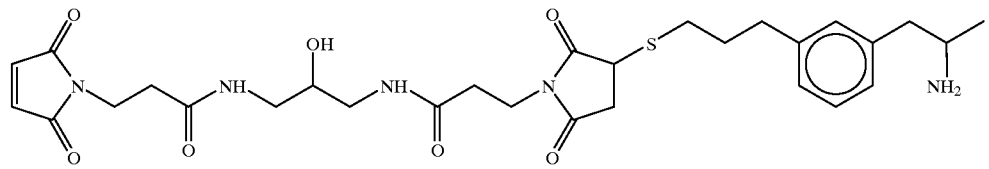

Methamphetamine protein conjugates were prepared by using an activated methamphetamine derivative of the following, structure (BMP-methamphetamine):

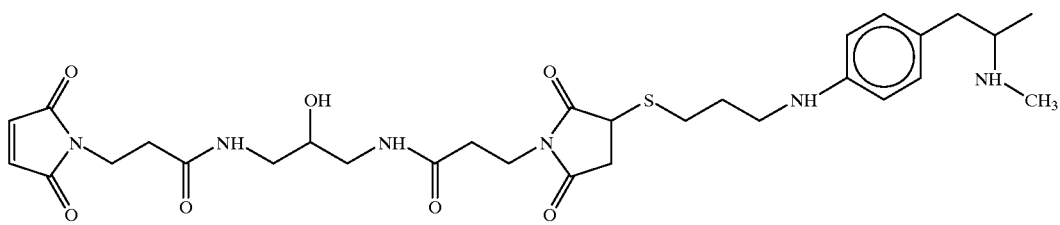

The derivatives were prepared by synthesizing p-3-mercaptopropylamino-d-methamphetamine, and meta-3-mercaptopropyl-d-amphetamine according to the methods described in U.S. Pat. No. 5,470,997 (Buechler et al.). U.S. Pat. No. 5,470,997 is hereby incorporated herein by reference in its entirety.

Immunogens were prepared by linking the derivative to KLH. The KLH was pre-thiolated according to the following procedure. One vial of KLH (20 mg, Pierce) was combined with 2 mL water, and vortexed to dissolve. 1 mL of the solution was combined with 10 mg of 2-iminothiolane (2-IT, Traut's reagent) and vortexed. The solution was incubated at room temperature for ~1 hour, after which 1.5 mL of 50 mM phosphate buffer (pH 8.0) was added. Unreacted reagent was removed on a PD-10 pre-packed Sephadex® G-25 ion exchange column (Pharmacia, Inc.). The presence of active SH groups on the recovered KLH was confirmed before use in the next step.

To perform the conjugation, 6 μmol (660 eq) of BME-amphetamine was dissolved in 750 μL of DMF. The solution of thiolated KLH was added; the mixture was vortexed, and then incubated for 1 hour at room temperature. To confirm conjugation, 200 μL of the mixture (or 200 μL 50 mM phosphate buffer pH 7.0 as control) was reduced with Ellman's reagent. Essentially all available SH groups on the KLH had reacted with BME-amphetamine, since excess maleimide was detected. The product was dialyzed 3 times against 10 L of deionized water, and then freeze-dried. Monoclonal antibodies were raised against the immunogens, and hybridoma supernatants were screened in a cloned β-galactosidase enzyme donor assays for the desired activity and specificity.

Conjugated enzyme donors were prepared by linking the activated derivative to the sulfhydryl group of the enzyme donor ED28. To a solution of desalted ED28 (1 mg, 102 nmole) in 100 mM sodium phosphate buffer (2.3 ml, pH=7.0) was added BMP-amphetamine (0.44 mg, 612 nmole) or BMP-methamphetamine (0.46 mg) in DMF (200 μl). The solution was vortexed for 30 seconds, and allowed to stand for 2 hours. A PD-10 column was pre-equilibrated with 0.1% TFA in water. The conjugate was desalted on this column, and further purified by HPLC. The purified solution was stored at −70° C. until further use.

A diagnostic-grade homogeneous enzyme assay kit for detecting either amphetamine or methamphetamine in a biological sample is widely available under the name CEDIA® DAU Amphetamines.

In the CEDIA® DAU Amphetamines assay, Reagent 1(R1) contains enzyme acceptor (EA), and the test antibodies specific for amphetamine and methamphetamine. Reagent 2 (R2) contains enzyme donor (ED)-amphetamine and ED-methamphetamine conjugates and chlorophenol-red-β-D-galactopyranoside (CPRG) as substrate. In this test, sample (3 μL of calibrator, control or unknown) and 130 μL of R1 are added to the cuvette of a clinical chemistry analyzer and incubated at 37° C. for 5 minutes. During this incubation any amphetamine or methamphetamine present in the sample will bind to their respective test antibodies. Subsequently 130 μL of R2 is added to the cuvette, mixed and incubated at 37° C. for 4 minutes. During this period, ED-amphetamine and -methamphetamine conjugates bind to their respective test antibodies. Any ED-drug conjugate remaining unbound will react with EA to form active enzyme. The amount of active enzyme formed will increase if drug from the sample occupies some of the antibody binding sites. The amount of enzyme is then determined from 4 to 5 minutes after R2 addition as the rate of CPRG hydrolysis, measured by the rate of change in absorbance at 570 nm.

The antibodies for the CEDIA® DAU Amphetamines Test are on deposit with the American Type Culture Collection (ATCC), under the following designations: Amphetamine—Safe Deposit #2004; Methamphetamine—Safe Deposit #2009.

Example 2

Conjugates With a Linkage to the Amphetamine Alkyl Amide Group

Amphetamine conjugates linked through the aromatic ring show high cross-reactivity with ring substituted analogs. It has been found that linkage of the hapten through the nitrogen group elicits antibodies that discriminate between unsubstituted amphetamines and similar compounds.

The synthesis of N-butylmaleimide-amphetamine was accomplished by first preparing the key intermediate, N-butylamine-amphetamine (AMP-BA):

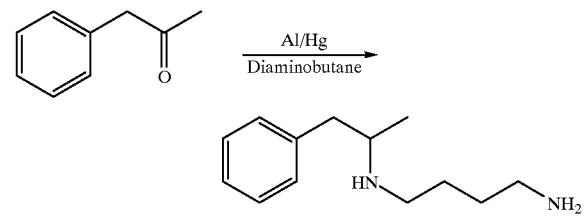

A synthesis of this material has been described previously (G. J. Turner et al., *Ann. Clin. Biochem.* 1991, 28, 588–94) but the preparation described here is experimentally simpler, provides better yield, is more amenable to scale-up, and does not start with amphetamine. The starting material for this synthesis was commercially available methyl benzyl ketone.

Mercuric chloride (200 mg) dissolved in ethanol (10 ml) was added to aluminum foil strips (10 g) in IPA (300 ml) with water (10 ml) contained in a 1 L round bottom flask. Diaminobutane (32.9 g) was added followed by methyl benzyl ketone (10 g) in IPA (50 ml). After 50 minutes the flask was placed in a 80° C. water bath for 105 minutes. After standing overnight at room temperature, the gray slurry was suction filtered through Celite. The filter cake was further extracted with methanol (150 ml). The filtrate was concentrated and 6 N HCl (75 ml) added. This mixture was washed with ether (3×50 ml) to remove unreacted ketone. The aqueous solution was basified with 10 N NaOH (50 ml) and extracted with toluene (3×75 ml). The toluene solution was dried with $NaSO_4$ and concentrated to yield a pale amber oil (9 g, 59% yield). This oil was distilled under reduced pressure (105–125° C./1 torr) to yield AMP-BA (N-butylamine-amphetamine) as a pale yellow oil (7 g, 45% yield).

The structure was confirmed by MS, $^1$H-NMR, and $^{13}$C-NMR: $^1$H NMR (200 MHz, $CD_3CN$) ppm 7.30 (5H, m, ArH), 2.80 (2H, m, $ArCH_2$), 2.70 (1H, m, $ArCH_2CH$), 2.55 (4H, m, $NCH_2R$), 1.35 (4H, m, $NCH_2CH_2$), 1.2 (3H, d, Me). $^{13}$C NMR(50 MHz, $CD_3CN$) ppm 140.2, 129.8, 128.9, 126.7, 55.0, 46.7, 42.9, 41.2, 30.1, 27.2, 19.1. MS-EI (AMP-BA-$TMS_2$): m/z 335 ($M^+$-15; α loss of methyl), 259 (M-91; neutral of $C_7H_7$ phenyl charge retention on side-chain); (AMP-BA-TBDMS): m/z 305 ($M^+$-15, α loss of methyl), 263 (M-57, α loss of t-butyl), 229 (M-91; neutral of $C_7H_7$ phenyl charge retention on side-chain).

The N-butylamine-amphetamine (AMP-BA) was converted into the maleimide derivative N-butylmaleimide-amphetamine (AMP-BM) as follows:

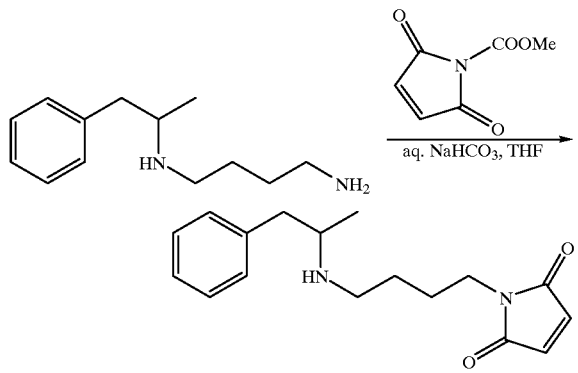

AMP-BA (206 mg) was dissolved in THF (10 ml) in a round bottom flask and cooled in an ice bath. Saturated $NaHCO_3$ solution (5 ml) was added. Ten minutes later methoxycarbonyl maleimide (155 mg) was added. After stirring for 110 minutes water (5 ml) was added and the mixture extracted with EtOAc (3×5 ml). The organic extract was washed with brine (5 ml) and dried with $MgSO_4$. Trifluoroacetic acid (75 μl, TFA) was added and the solution concentrated to yield crude AMP-BM as a cream colored solid (292 mg, 73% yield). A portion of the crude AMP-BM (5 mg) was purified by injecting a solution in 20 mM TFA in water (1 ml) into a HPLC (C4 1×25 cm, 0 min, 100% A (20 mM TFA in water); 0.1–20 min, 15–25% B (20 mM TFA in MeCN); flow rate=4 ml/min, 260 nm) via a 2 ml loop to yield pure AMP-BM-tfa (N-butylmaleimide-amphetamine trilluoroacetate) as a fluffy white solid (3.6 mg) after lyophilization.

The structure was confirmed by $^1$H-NMR: $^1$H NMR (200 MHz, $CD_3CN$, AMP-BM-tfa) ppm 7.30 (5H, m, ArH), 6.85 (2H, s, olefin), 3.45 (2H, m, $CH_2NCO$), 3.15 (2H, m, $ArCH_2$), 3.00 (2H, m, $NCH_2R$), 2.75 (1H, m, $ArCH_2CH_2$), 1.2 (3H, D, Me).

An immunogen (KLH-2-IT-BM-AMP) was prepared by first reacting KLH with 2-iminothiolane (2-IT) followed by reaction with N-butylmaleimide-amphetamine:

2-Iminothiolane (2-IT) (2.75 mg) was added to KLH (20 mg) in phosphate buffer (2 ml, 83 mM, pH=7.2, 0.9 M NaCl) with stirring. After 105 min phosphate buffer (500 μl, 100 mM, pH=7) was added to the mixture and desalted with a PD-10 pre-packed SEPHADEX G-25 ion exchange column (Pharmacia, Inc.) pre-equilibrated with phosphate buffer (100 mM, pH=7) to remove excess 2-IT. The eluant (3 ml) was added to AMP-BM-tfa (3.20 mg) in DMF (1 ml). After stirring for 5 hours the mixture was dialyzed against phosphate buffer (800 ml, 10 mM, pH=7, 150 mM NaCl) and DMF (200 ml). After 12 hours the buffer was replaced. After an additional 12 hours this buffer was replaced with phosphate buffer (2 L, 10 mM, pH=7, 150 mM NaCl) which was again replaced after another 12 hours. Twelve hours after the last buffer replacement the immunogen (6 ml) was transferred to a vial and stored at −80° C. until used.

An enzyme conjugate (ED28-BM-AMP) was prepared by reaction of AMP-BM with the enzyme donor ED28:

A solution of desalted ED28 (1 mg) in phosphate buffer (234 μl, 100 mM, pH=7) was added with stirring to a solution of AMP-BM-tfa (245 μg) in DMF (180 μl). After standing at room temperature for 100 minutes TFA in water (116 μl, 20 mM) was added and the mixture desalted on a NAP-10 pre-packed SEPHADEX G-25 ion exchange column (Pharmacia, Inc.) pre-equilibrated with 20 mM TFA in water. TFA in water (1 ml, 20 mM) was added to the eluant (1 ml) and half the solution was injected in a 2 ml loop and purified by HPLC (C4 1×25 cm, 0 min, 100% A; 0.1–20 min, 25–45% B, flow rate=4 ml/min; 280 nm. The purification was repeated to afford a total of 8.9 ml of eluant. The yield was 677 μg (63%) as determined by UV absorbance at 280 nm ($\epsilon_{280}$=16,000). This solution was stored at −80° C. until further use.

Example 3

Antibodies that Neutralize Both Amphetamine and Methamphetamine

Monoclonal antibodies were obtained by immunizing and boosting mice with the KLH-BM-AMP immunogen. After sufficient time for an immune response to develop, mouse spleen lymphocytes were fused to mouse myeloma cells, and the resulting hybridoma cells were cloned by limiting dilution. Antibody-secreting cell lines with the desired specificity were identified in a double screening process using a CEDIA® type immunoassay.

Antibodies were initially selected for their ability to bind amphetamine attached to the BM-AMP enzyme donor. Supernatants were screened tell days post-fusion for inhibition of the corresponding ED-amphetamine-butyl maleimide conjugate in a cloned β-galactosidase enzyme donor immunoassay. 50 μL hybridoma supernatant was transferred to each well of a 96-well plate. 75 μL EA-22 (25 U/ml) in Assay Buffer (30 mM K phosphate. monobasic; 30 mM K phosphate, dibasic; 400 mM NaCl; 10 mM EGTA; 0.05% Tween™20; 2 mM Mg Acetate; 0.02% NaN₃ was added to each well, and the plates were incubated for 15 min at room temp. Next, 75 μL of reagent containing the BM-AMP enzyme donor (1 nM), GAMS (goat anti-mouse IgG; 1/200 dilution), and the enzyme substrate CPRG (0.5 mg/ml) in Assay Buffer were added to each well. After a further one hour incubation at room temperature, the optical density was read at 540 nm with a 690 nm reference wavelength.

Hybridoma wells giving >25% inhibition of enzyme formation (as compared with a culture medium control) were cloned by serial dilution. The antibodies were initially screened for their ability to neutralize both amphetamine and methamphetamine in the CEDIA dual assay system for amphetamine and methamphetaminie. Over 20 MAb anti-amphetamine antibodies from 3 different fusions have been evaluated.

The procedure was as follows: cell supernatants were concentrated to 3 times their normal concentration by centrifugation through a 30,000 Dalton filter. Reagents from a CEDIA® amphetamine kit were reconstituted according to manufacturer's directions. To the R1 (antibody reagent) either a blank supernatant or the antibody supernatant was added, using 4 parts reagent to 1 part supernatant (1:5 dilution). The assay was performed using 6 calibrators.

Hybridomas were selected that could neutralize both amphetamine and methamphetamine calibrator samples, without inhibiting the reaction between the enzyme donor and acceptor. The criteria were as follows: a) a depression of rate of at least 10 mA/min for amphetamine at 1000 ng/ml compared with control; b) a depression of rate of at least 20 mA/min for methamphetamine at 1000 ng/ml compared with control; as measured; c) no significant rate shift (more than 10%) for the 0 ng/ml calibrator or the 60,000 ng/ml calibrator. The criteria were set very loosely as the concentration of antibody in these cell supernatants was unknown and we did not want to prematurely eliminate any of them.

A second screening step was performed to eliminate antibodies with a high cross-reactivity to fenfluramine. Fenfluramine is a drug that commonly results in a false positive result in amphetamine testing. Its cross-reactivity in the CEDIA® amphetamine assay is 37%.

Hybridomas that survived at least three rounds of cloning and had response to amphetamine and methamphetamine were produced from ascites fluid for further evaluation. Antibodies designated 7B3, 5D10, 8E5, 11G6, 14B2, and 12B5 were chosen that initially showed good amphetamine binding or neutralization, and little cross-reactivity with fenfluramine. Antibody 2E12 was chosen even though there wag a degree of cross-reactivity, because of an exceptional quenching activity for both amphetamine and methamphetamnine. Antibody 10F12 was chosen, even though it initially showed poor neutralization, because of excellent ability to distinguish amphetamine from fenfluramine.

Antibody was purified from ascites and tested at concentrations of 50, 100, 150, 200, and 300 μg/ml. The results are shown in the following table:

TABLE 2

Screening of Neutralizing Antibodies for Amphetamines Assay

| | | Candidate Antibody (200 μg/ml) | | | | | | |
|---|---|---|---|---|---|---|---|---|
| | | 7B3 | 2E12 | 5D10 | 8E5 | 11G6 | 14B2 | 12B5 |
| | | Mean Rate, mA/min | | | | | | |
| Amp A | 0 ng/ml | 140.4 | 149.9 | 140.5 | 134.9 | 146.3 | 146.2 | 150.2 |
| Amp C | 500 | 146.0 | 153.6 | 177.6 | 169.4 | 156.9 | 157.3 | 163.1 |
| Amp F | 1000 | 150.9 | 159.0 | 203.4 | 189.7 | 166.0 | 168.7 | 172.6 |
| Amp I | 3000 | 173.3 | 175.4 | 245.9 | 233.8 | 195.9 | 196.3 | 202.3 |
| Amp K | 5000 | 189.8 | 191.8 | 272.6 | 257.3 | 216.2 | 218.7 | 223.1 |
| Meth C | 500 | 141.1 | 152.2 | 154.7 | 147.5 | 152.5 | 153.2 | 151.3 |
| Meth F | 1000 | 145.8 | 158.4 | 167.6 | 164.0 | 160.6 | 160.4 | 154.4 |
| Meth I | 3000 | 162.9 | 168.4 | 209.6 | 214.4 | 188.1 | 186.2 | 162.3 |
| Meth K | 5000 | 183.1 | 181.6 | 245.7 | 251.0 | 213.7 | 214.3 | 173.0 |
| (open) | 60000 | 611.2 | 644.0 | 617.0 | 597.1 | 628.4 | 635.7 | 623.2 |
| | | Calculated Dose, ng/ml | | | | | | |
| Amp A | 0 ng/ml | −27 | −55 | −129 | −65 | −71 | −31 | 36 |
| Amp C | 500 | 24 | −25 | 181 | 250 | 14 | 56 | 95 |
| Amp F | 1000 | 68 | 17 | 396 | 436 | 86 | 146 | 222 |
| Amp I | 3000 | 272 | 148 | 2022 | 1299 | 325 | 362 | 473 |
| Amp K | 5000 | 423 | 278 | 2457 | 2199 | 486 | 570 | 641 |
| Meth C | 500 | −21 | −37 | −10 | 50 | −22 | 24 | 46 |
| Meth F | 1000 | 22 | 13 | 98 | 201 | 43 | 81 | 71 |
| Meth I | 3000 | 178 | 92 | 448 | 802 | 262 | 283 | 137 |
| Meth K | 5000 | 362 | 197 | 2019 | 1958 | 467 | 506 | 568 |

The best neutralization was observed from the 2E12 antibody, and 7B3, 11G6, 14B2, and 12B5 remained good candidates. Antibodies 5D10 and 8E5 are poor neutralizers and were eliminated. Final selection is made by testing with a panel of clinically obtained urine samples containing an amphetamine or an interfering substance.

Example 4
Homogeneous Bidirectional Confirmation Assay for Amphetamine

In this example, a homogeneous confirmation assay was developed based on the CEDIA® DAU Amphetamines assay.

Figure 1:
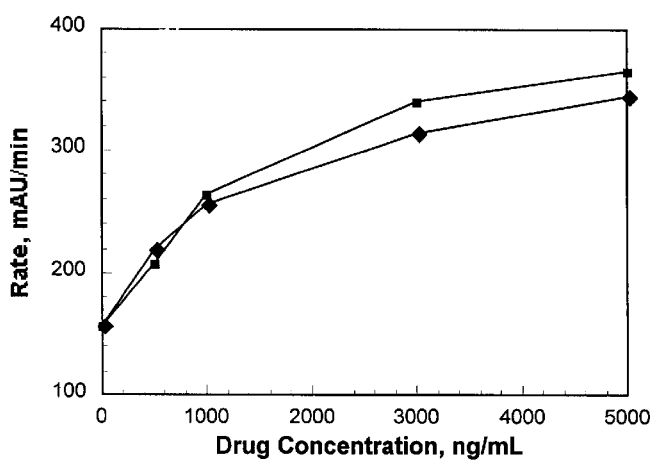
FIG. 1 is a series of three graphs illustrating a bidirectional antibody type confirmation assay for amphetamines. The upper graph shows a typical standard curve for amphetamine (♦) and methamphetamine in a homogeneous assay. The exemplar is an enzyme complementation assay commercially available in the CEDIA® DAU product line.
Figure 1:
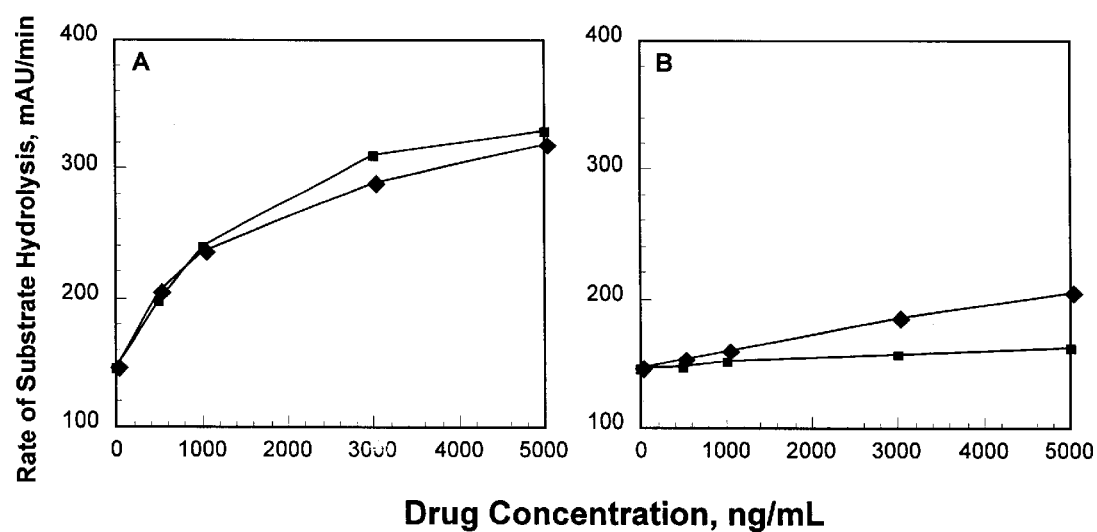

FIG. 1 (Upper Panel) shows a typical standard curve for amphetamine and methamphetamine using the CEDIA® DAU Amphetamines assay. Enzyme activity, as measured by the rate of change of absorbance at 570 nm (in mAU/min) was determined as a function of amphetamine (♦) or methamphetamine (■) concentration. In this test, a sample is considered positive if the rate is equal to or greater than that of the 1000 ng/ml amphetamine calibrator. A second protocol is available which uses a 6 μL sample volume; in this case, the decision point is at 500 ng/ml amphetamine.

The confirmation test for amphetamines was developed by addition of the absorbing antibody to the R1 of the existing test, until the change in rate by up to 5000 ng/ml added amphetamine or methamphetamine is reduced to below the change in rate due to the cut-off (1000 ng/ml) calibrator in the unmodified test. Antibody 12B5 (300 μg/ml) was added to R1 of the CEDIA® DAU Amphetamines assay, and the effect on the amphetamine and methamphetamine standard curves obtained using the assay reagents was determined.

FIG. 1 (Lower Panel) shows the effects of the absorbing antibody on signal due to amphetamine (♦) and methamphetamine (■). Panel A shows the result from the unmodified assay; Panel B shows the effect of including the neutralizing antibody in the reaction mixture.

At higher concentrations of amphetamine or methamphetamine than those shown in the figure, the amount of drug exceeds the binding capacity of the absorbing antibody. In this example, the rates obtained at 60,000 ng/ml methamphetamine in the absence and presence of absorbing antibody 12B5 were 607 and 602 mAU/min, respectively. Therefore, above a certain empirically-determined rate in the unmodified test, an unknown sample is further tested by GC/MS regardless of the result in the confirmatory immunoassay. With absorbing antibody 12B5 at 300 μg/ml, this point was determined to be the rate produced by a calibrator containing 8,000 ng/ml methamphetamine.

FIG. 2 shows the results of several potential interfering substances. Effect of absorbing antibody on response of the CEDIA DAU Amphetamines assay to cross-reactive substances. Varying concentrations of pseudoephedrine (Panel A), phenylpropanolamine (Panel B), phentermine (Panel C) and tyramine (Panel D) were dissolved in urine and tested as samples in the absence (♦) and presence (■) of absorbing antibody 12B5 (300 μg/ml in Reagent 1).

The concentrations of pseudoephedrine, phenylpropanolamine, phentermine and tyramine needed to give a positive result (rate≧the rate of the 1000 ng/ml amphetamine calibrator) are 203, 582, 59.1 and 98.5 μg/ml, respectively. The high concentrations needed to give a positive rate indicate the high degree of specificity exhibited by the test antibodies in the unmodified CEDIA® DAU Amphetamines assay. However, these compounds can be found in the urine at extremely high concentrations, resulting in false positive results during drugs of abuse screening. Very high concentrations of cross-reactants can also decrease the ability of the neutralizing antibody to lower the signal due to the target analyte. The concentrations of pseudoephedrine, phenylpropanolaminie, phentermine and tyramine needed to give a positive result in the CEDIA® DAU Amphetamine confirmatory test are 243,708, 70.6 and 97.9 μg/ml, respectively. These concentrations are equal to or slightly above the concentrations required for a positive result observed in the absence of neutralizing, antibody.

The amphetamine confirmatory assay was tested with a panel of actual urine samples obtained from a drug screening laboratory. The test samples were chosen as positive in the CEDIA® DAU Amphetamines assay, based on a delta rate greater than that of the 1000 ng/ml amphetamine calibrator. Samples with rates above that of an 8,000 ng/ml methamphetamine calibrator were excluded from the test panel, since these samples are more optimally processed for GC/MS regardless of the result in the immunoassay. Out of 96 samples meeting this threshold in the standard CEDIA® DAU Amphetamines assay, 94 were confirmed positive by GC/MS, while 2 were false positive. This is a typical observation, since it is unlikely that cross-reactive substances will be present in the extremely high concentrations needed to give a signal equivalent to 8,000 ng/ml methamphetamine.

Samples in the test panel with rates between 1000 and 8000 ng/ml were pre-evaluated by GC/MS. A sample was classified as true positive if it met one of the following criteria: either ≧500 ng/ml methamphetaminine and ≧200 ng/ml of amphetamine; or ≧500 ng/ml of amphetamine. Samples were considered false positive if they failed to meet either of these criteria by GC/MS.

The result of the confirmatory test were calculated as the rate in the standard test channel (the normal CEDIA® DAU Amphetamines assay) minus the rate in the confirmatory test channel (CEDIA® DAU Amphetamines assay, plus absorbing antibody added to R1). The results are presented in the following table as Δ Rate Units, in mAU/min.

TABLE 3

Effect of Absorbing Antibody on Rates of True and False Positive Samples

| Confirmatory assay result Δ Rate mAU/min | Number of True Positives | Number of False Positives |
|---|---|---|
| <10 | 0 | 32 |
| ≧10, <15 | 0 | 3 |
| ≧15, <20 | 0 | 3 |
| ≧20, <25 | 0 | 9 |
| ≧25, <30 | 1 | 2 |
| ≧30, <40 | 1 | 1 |
| ≧40, <50 | 0 | 1 |
| ≧50 | 101 | 2 |
| Total | 103 | 53 |

These results show that by using a Δ Rate selection criterion of ≧25, the number of false positive samples in this group is reduced by 84%. For an unknown sample, the early elimination of false positives using a confirmatory assay saves the necessity of testing them by GC/MS, resulting in a substantial cost savings.

The confirmatory test approach can be used for other drug of abuse tests, including those where the results are reported as a qualitative result. The method is particularly advantageous for high-volume screening methods, as exemplified by such homogeneous test methods as the CEDIA®, Emit and latex microparticle tests, and heterogeneous test methods such as ELISA.

Example 5
Detecting Antibodies and Assays for LSD

The commercially available CEDIA® DAU LSD kit contains the LSD-specific monoclonal antibody designated 19A7, and an N-1 carboxyalkyl LSD enzyme donor conjugate. The preparation of these reagents is described fully in International patent application PCT/US 96/19266.

Briefly, N-1-(ethyl-carboxymethyl)-LSD was prepared as a starting material by treating LSD with a molar excess of sodium hydride followed by the addition of ethylbromoacetate. The product was isolated by preparative HPLC on a 2.2×25 cm C4 column using 0–10 min, 10% acetonitrile/0.1 M TEA-Ac; 10–60 min, 10–60% acetonitrile/0.1 M TEA-Ac: 60–65 min, 65% acetonitrile/0.1 M TEA-Ac; 65–75 min, 10% acetonitrile/0.1 M TEA-Ac. The desired product eluted toward the end of the gradient with a back shoulder, corresponding to partially resolved N-1-(ethyl-carboxymethyl)-isoLSD. Fractions free of the isoLSD) shoulder were pooled and lyophilized. The pooled fraction was analyzed by $^1$H-NMR in acetonitrile-$d_3$ and identity confirmed by mass spectrometry (MS).

The N-1-(ethyl-carboxymethyl)-LSD was then hydrolyzed to yield N-1-carboxymethyl-LSD (N-1-CM-LSD). 28.5 mg, 70 μmol was dissolved in 3.5 ml of ethanol, the reaction vial was purged with argon gas, and, 75 μl of a 1N NaOH was then injected with stirring. The reaction was monitored using the analytical system described above for preparing the starting material. The product eluted at about 24–25% acetonitrile as a sharp peak. The reaction mixture was then neutralized by adding one equivalent of acetic acid and 1 ml of water, and the resulting solution was clear. The product was isolated and desalted by HPLC on a preparative C4 column using 20 mM TEA-Ac, pH 7, and acetonitrile according to the following program: 0–5 min, 0% acetonitrile/20 mM TEA-Ac; 5–55 min, 0–50% acetonitrile/20 mM TEA-Ac; 55–60 min, 100% acetonitrile. The flow rate was 8 ml/min. The major peak, which eluted around 28–29% acetonitrile, was collected and fractions changed on the back side of the peak to eliminate any shoulder for isoLSD derivative. The pooled fractions were lyophilized and re-lyophilized 2 times from water/acetonitrile 4:1 to get rid of the TEA-Ac and convert the product to a zwitterion. The pooled fraction was analyzed by $^1$H-NMR in acetonitrile-$d_3$ and identity confirmed by mass spectrometry (MS).

N-1-(carboxymethyl) LSD N-hydroxysuccinimide ester (N-1-CM-LSD-NHS) was prepared by dissolving a sample of N-1-carboxymethyl-LSD (6.6 mg) in 1.0 ml DMSO. To that solution N-hydroxysuccinimide (NHS) (14 mg) and 1-ethyl-3-(3-dimethylaminopropyl)carbodiimide hydrochloride (EDC) (23.2 mg) was added. The solution was vortexed and incubated at ambient temperature overnight. The activated N-1-CM-LSD-NHS was used in for the next step without further purification.

KLH conjugates were formed as follows: N-1-CM-LSD-NHS (5.7 mg) in 1.0 ml DMSO was added to 15.0 mg KLH in 4.0 ml phosphate buffer, vortexed gently for two minutes and allowed to stand at ambient temperature for 8.0 hours.

A second conjugate was prepared using a maleimidoethylamine (MEA) derivative. A 2-fold excess of MEA HCl (6.1 mg) in 1.5 ml phosphate buffer was added to the activated N-1-CM-LSD-NHS. The progress of the reaction was monitored by HPLC. The N-1-MEA-CM-LSD was purified by HPLC. Thiolated KLH (7.0 mg, prepared as described elsewhere this disclosure in 2.1 ml of phosphate buffer was added to a solution of N-1-MEA-CM-LSD (3.5 mg) in DMSO (0.60 ml). The resulting solution was vortexed gently for two minutes and allowed to stand at ambient temperature for 5 hours. The immunogens were dialyzed against water/MeOH (80:20 v/v) for three days.

An LSD enzyme donor conjugate was prepared as follows: To a solution of N-1-CM-LSD-NHS (50.11 mg) an approximately equivalent number of moles of maleimidopentylamine hydrochloride (MPA) (28.78 mg) in DMF was added. To keep the reaction mixture at neutral pH, 300 μl of triethylamine (TEA) was added and the pH checked. The progress of the reaction was monitored by HPLC. The N-1-MPA-CM-LSD was then HPLC purified and used in the preparation of the ED conjugate. A solution of thiolated ED28 (5.0 mg) was prepared and desalted in 3.5 ml phosphate buffer. This solution was then added to the solution of N-1-MPA-CM-LSD (1.67 mg/1.5 ml DMF). The resulting mixture was vortexed gently for 2 minutes and allowed to stand at ambient temperature for 55 min. The protein conjugate N-1-MPA-CM-LSD:ED was HPLC purified.

Monoclonal antibodies were raised using the KLH conjugates according to the methods described elsewhere in this disclosure. A primary screening of the fusion products was first performed to evaluate the ability of the antibodies to bind to the enzyme donor conjugate. The number of inhibition-positive clones were then narrowed further by performing a secondary screening assay to determine whether the free drug would modulate or compete with the enzyme donor conjugate for the antibody. The modulation assay also identified specific clones when screened against cross-reacting analytes.

A model CEDIA® assay for LSD was performed using the following reagents. Antibody reagent: test antibody, 57 ng/ml; 100 mM PIPES 100; 500 mM NaCl, 0.5% fetal bovine serum, 10 mM EGTA, 10 mM magnesium acetate, 20 mM sodium azide; pH 6.9. Enzyme donor reagent: 0.487 nM conjugate; 3 mg/ml of the substrate CPRG (chlorphenyl-red-β-D-galactopyranoside); 100 mM PIPES; 400 mM NaCl, 10 mM EGTA, 2 mg/ml fragmented BSA, 20 mM sodium azide; pH 6.9. Enzyme acceptor reagent: acceptor 880 U/ml; magnesium acetate 10 mM, NaCl 400 nM, PIPES 100 nM, EGTA 10 mM, sodium azide 20 mM, pH 6.9.

Assays were performed using an HITACHI 911 analyzer. The absorbance rate at 570 nm was plotted against LSD concentration to construct a dose response curve. Several antibody clones were identified with sensitivity and specificity suitable for use in a CEDIA® format LSD assay.

Example 6
Neutralizing Antibodies for LSD

The LSD-enzyme donor conjugate of the previous example is a conjugate in which LSD is linked through the N-1 position.

Neutralizing antibodies for LSD for use in a bidirectional type confirmation assay are prepared using an LSD derivative in which the LSD is linked to an immunogenic carrier by the alkyl amide group.

The following scheme shows the preparation of KLH-amino-N-(3-carbonylpropyl)-N-ethyl lysergamide:

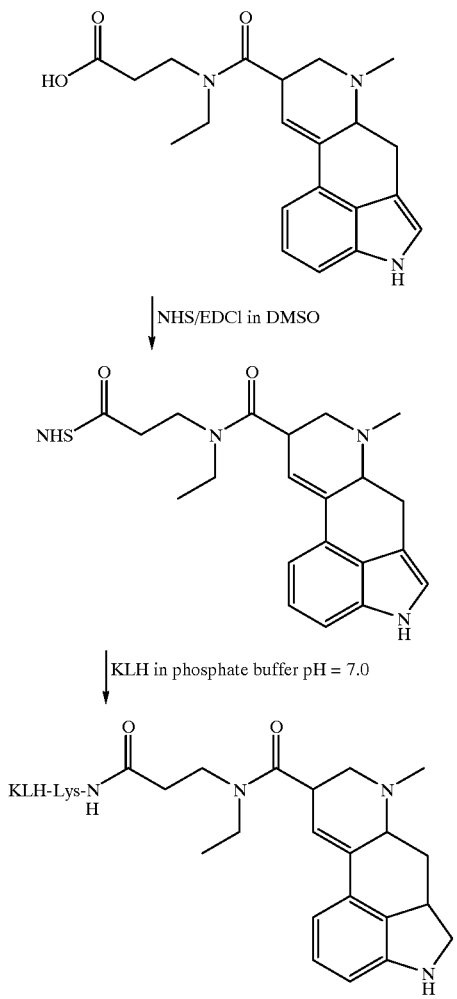

N-(3-Carboxypropyl)-N-ethyl lysergamide was activated to N-(O-succinimido-3-carbonylpropyl)-N-ethyl lysergamide as follows:

Sure-Seal™ DMSO (0.3 ml) was transferred into an appropriately sized glass vial. The solution was flushed with a flow of argon. N-(3-Carboxypropyl)-N-ethyl lysergamide (4.1 mg), N-hydroxy succinimide (5.6 mg) and 1-Ethyl-3-(3-Dimethlyaminopropyl)carbodiimide Hydrochloride (EDCI) (8.2 mg) was added to the vial. A dry magnetic stirrer bar was placed in the reaction mixture. The solution was stirred at room temperature for 4.5 hrs. At this point, a 10 µl aliquot of the reaction mixture was taken, and diluted with 90 µl $H_2O$ containing 0.1% of trifluoroacetic acid. The sample (50 µl) was analyzed by HPLC. The HPLC results indicated a 88% conversion of the starting acid to the NHS active ester. The reaction mixture was incubated for additional 1 hr.

The immunogen KLH-[amino-N-(3-carbonylpropyl)-N-ethyl lysergamide]$_n$ was prepared as follows:

To a solution of KLH (10 mg) in Phosphate buffer (1 ml, 50 mM, pH=7.0) was added 0.2 ml of DMSO. The N-(O-succinimido-3-carbonylpropyl)-N-ethyl lysergamide was added to the KLH solution dropwise while vortexing the solution. After the final addition, the immunogen solution was kept at room temperature overnight. The immunogen solution was transferred into a dialysis tube and dialyzed in 800 ml of water and 200 ml of DMF in a cold room overnight. The immunogen was dialyzed two more times, with 4000 ml of deionized water within two days.

The number of (3-carbonylpropyl)-N-ethyl lysergamide molecules per KLH was determined as follows:

One milligram of KLH-[amino-N-(3-carbonylpropyl)-N-ethyl lysergamide]$_n$ was dissolved in 1.0 ml of 1.0N NaOH. The UV-Visible spectrum of the solution was recorded between 200–400 nm against the same solvent as reference. Using the extinction coefficient of 5,899 $M^{-1}$ $cm^{-1}$ at 320 nm for N-(3-Carboxypropyl)-N-ethyl lysergamide (where there is negligible absorption for KLH), the molar ratio was calculated to be 242.

Mice are injected with this immunogen and splenocytes are harvested for the production of monoclonal antibodies. Initial screening is performed in a similar fashion to that described for the screening of the amphetamine neutralizing antibody in Example 2, using an enzyme donor conjugated with LSD at the same position as the immunogen. The selected antibody can then be used in a homogeneous confirmation assay for LSD, similar to the amphetamine confirmation assay described in Example 4.

Neutralizing antibodies for LSD for use in an adsorption type confirmation assay are prepared by insolubilizing the same 19A7 antibody used as the detecting antibody. Antibody 19A7 was purified by Protein A affinity chromatography, and then attached to cyanogen bromide-activated Sepharose® CL-4B (Pharmacia, Piscataway, N.J.) as recommended by the manufacturer. The resin was prepared to contain approximately 0.8 mg of bound antibody per ml of resin bed volume.

The procedure was as follows: The required amount of activated Sepharose® was weighed, taking into account that 1 g freeze-dried material swells to 3.5 ml gel volume. The gel was reconstituted and washed in wash buffer (1 mM HCl) (3 ml and then 200 ml per gram), and then washed in coupling buffer (0.1 M $NaHCO_3$, 0.5 M NaCl, pH 8.3) (50 ml per gram) using a Buchner funnel. The antibody was dissolved or exchanged into coupling buffer, and 5–10 mg were coupled per ml. The gel cake was transferred to a suitably sized container, the antibody was added, and the volume was adjusted to make a 50% slurry. The suspension was mixed end-over-end for 2 h at room temperature, or overnight at 2 to 8° C. (Stirring is avoided to prevent shearing of the beads.) The proportion of antibody successfully coupled was determined by measuring $A_{280}$ before and after coupling. Blocking buffer was then added (1M ethanolamine pH 8.0, or 0.2M Tris buffer, pH 8.0), and the suspension was mixed end-over-end for a further 2 h at room temperature, or overnight at 2 to 8° C. The gel was washed in a Buchner funnel with coupling buffer, second wash buffer (0.1 M Acetate, 0.5 M NaCl, pH 4.0), and then coupling buffer (100 ml each per gram).

The affinity resin was diluted with prepared inactivated Sepharose® 4B to yield the desired binding capacity. One and a half times the desired volume of Sepharose® 4B was transferred to a Buchner funnel, and washed with distilled water followed by storage buffer (400 ml and 200 ml per 50 ml gel). The washed gel was then added to the affinity resin. The theoretical binding capacity (in ng analyte per ml gel) was calculated assuming a molecular weight of 150,000 g/mol for IgG, a valence of 2 analyte molecules per IgG, negligible loss of activity due to coupling, and a molecular weight for LSD of 323.4. The resin is adjusted so that 10 μl resin provides sufficient antibody to adsorb LSD from the samples within the working range of the assay, but not a large excess. By calculation, 10 μL of resin can adsorb about 17 ng LSD, meaning that a 100 μL sample could contain about 170 ng/mL LSD. In practical terms, because of kinetic effects and other factors, samples above about 100 ng/ml will show significant but only partial adsorption.

Example 7
Adsorption Confirmation Assay for LSD

This example describes a solid-phase adsorption-type confirmation assay.

FIG. 3 (Upper Panel) provides an illustrative example of the use of solid-phase antibody 19A7 in a confirmation assay for LSD. Different concentrations of LSD were added to drug-free urine samples, and then these samples were tested in an unmodified CEDIA® DAU LSD assay (■). To conduct the confirmation assay, solid phase antibody (10 μL of a 1:2 dilution of the packed bed volume per 100 μL of sample) was added to each sample, incubated for 10 min at room temperature with mixing, and then allowed to settle. The samples were then retested in the CEDIA® DAU LSD assay (♦).

In this example, both the neutralizing antibody and the detecting antibody are monoclonal antibody 19A7.

The incubation of sample and resin can be carried out directly in the analyzer sample cup, by placing the sample and resin in the cup, covering with a seal (such as Parafilm®), and mixing, for example, on a rocking mixer such as is used in a hematology laboratory (such as the Thermolyne Vari-Mix platform mixer, available from Fisher Scientific, Pittsburgh, Pa.). Once the resin settles to the bottom of the reaction vessel, the supernatant can then be assayed. Alternatively, the resin can be separated from the sample using a chromatography column (e.g., PolyPrep column, BioRad Laboratories, Richmond, Calif.), or using or a filter with a suitable pore diameter.

This type of adsorption confirmation assay can be used to distinguish LSD from certain LSD metabolites.

FIG. 3 (Lower Panel) shows the results of an experiment in which varying concentrations of LSD (left Panel), 2-oxo-3-hydroxy LSD (Center Panel) or a partially-purified preparation containing a mixture of 13-hydroxy LSD glucuronide and 14-hydroxy LSD glucuronide (Right Panel) were added to drug-free urine samples. The samples were then tested in the unmodified CEDIA® DAU LSD assay (■) or after treatment with solid-phase antibody (♦).

The signal is completely eliminated by pretreatment with the solid phase antibody where the substance is LSD, and partially eliminated where the substance is one of the tested LSD metabolites. However, if desired, an absorbing antibody selected to not cross-react with metabolites could be attached to the solid phase. In this case, only parent drug would be absorbed, and samples which contained only metabolites would be read as false positive in the confirmation assay. This would be desired, for example, in the case where confirmation of the parent drug was a legal requirement.

In the CEDIA® DAU LSD assay, false positive results can be caused by high concentrations of drugs or drug metabolites, such as methamphetamine, fenfluramine and ambroxol. These drugs have very low cross-reactivities in the assay (0.0003%, 0.023% and 0.01%, respectively). However, due to the low concentration of LSD at its cut-off point, and the high concentrations of interfering substances that can be present in urine, a false positive result can be obtained for some samples.

FIG. 4 shows the effect of solid-phase antibody on assay response to drug cross-reactants. Different concentrations of methamphetamine (Left Panel), fenfluramine (Center Panel) or ambroxol (Right Panel) were added to drug-free urine samples. The samples were then tested in the unmodified CEDIA® DAU LSD assay (■) or after treatment with solid-phase antibody (♦).

Thus, the false positive results in the initial assay can be identified by the lack of absorption of cross-reactants using the solid-phase antibody.

In an enhanced version of the assay, relative rates are calculated to help distinguish between true positive and false positive samples. The first parameter is the net rate from the unmodified assay, and the second parameter is the difference between rates for the preadsorbed and the postadsorbed sample:

ΔRate 1=rate in the presence of sample minus the rate in the presence of a zero calibrator.

ΔRate 2=rate in the presence of sample minus the rate in the presence of sample after treatment with solid-phase antibody.

FIG. 5 (Upper Panel) shows the effect of solid-phase antibody on assay response to LSD and metabolites. Procedures are the same as for FIG. 4, but results have been calculated as ΔRates as described above: (■) ΔRate 1 (direct test); (♦) ΔRate 2 (confirmation test). In the left-most panel, results from the direct and confirmation test are superimposed.

FIG. 5 (Lower Panel) shows the effect of solid-phase antibody on assay response to drug cross-reactants. Procedures are the same as for FIG. 3 (Lower Panel), but results have been calculated as ΔRates as described above: (■) ΔRate 1 (direct test); (♦) ΔRate 2 (confirmation test).

Use of relative rates gives a more direct indication of the presence of LSD:

In the case of LSD, both ΔRate 1 and ΔRate 2 are positive, and so the sample is a true positive.

In the case of LSD metabolites, both ΔRate 1 and ΔRate 2 are also positive.

In the case of drug cross-reactants, ΔRate 1 is positive, but ΔRate 2 is close to zero, indicating a false positive.

The rate differences can be calculated manually, or by instrument software available with many automated clinical chemistry analyzers, such as the Boehringer Mannheim/Hitachi 911.

The secondary screening test was applied to a panel of true and false positive samples obtained from drug testing laboratories. All samples had tested positive in the CEDIA® DAU LSD assay (apparent LSD concentration≧0.5 ng/ml).

Results are summarized in the following Table:

TABLE 4

Effect of Solid-Phase Antibody on True and False Positive Samples

| Sample Type | Sample ID | CEDIA ® rate mAU/min | CEDIA ® Δ rate mAU/min | CEDIA ® LSD ng/ml | + RESIN rate mAU/min | + RESIN Δ rate mAU/min | GC/MS LSD ng/ml |
|---|---|---|---|---|---|---|---|
| Calibrator | LSD 0 | 125.8 | 0 | 0 | 124.6 | 1.2 | |
| | LSD 0.5 | 160.4 | 34.6 | 0.5 | 130.8 | 29.6 | |
| | LSD 1.5 | 209 | 83.2 | 1.5 | 125.4 | 83.7 | |
| | LSD 3.0 | 233.5 | 107.7 | 3 | 128.1 | 105.4 | |
| | LSD 10 | 238.2 | 112.4 | >3 | 218.9 | 19.3 | |
| False Positive | BM 1 | 177.5 | 51.7 | 0.85 | 169.5 | 8.1 | |
| | BM 5 | 158.9 | 33.1 | 0.48 | 148.2 | 10.8 | |
| | BM 13 | 173.1 | 47.3 | 0.76 | 167.9 | 5.2 | |
| | T850162 | 170.9 | 46.2 | 0.55 | 164.5 | 6.4 | |
| | T850163 | 163.4 | 38.7 | 0.49 | 150.9 | 12.5 | |
| True Positive | NWBL-12 | 199.1 | 73.3 | 1.3 | 173.7 | 25.4 | 0.23 |
| | NWBL-28 | 195.4 | 69.6 | 1.22 | 167.7 | 27.7 | 0.47 |
| | NWBL-05 | 158.4 | 32.6 | 0.47 | 128.4 | 30 | 0.23 |
| | NWBL-19 | 164.8 | 39 | 0.59 | 131.8 | 33.1 | 0.89 |
| | NWBL-21 | 164.3 | 38.5 | 0.58 | 129.1 | 35.2 | 0.79 |
| | NWBL-22 | 169.7 | 43.9 | 0.69 | 130.1 | 39.7 | 0.68 |
| | NWBL-15 | 168.9 | 43.1 | 0.67 | 129 | 39.9 | 0.74 |
| | NWBL-23 | 163.5 | 37.7 | 0.56 | 122.2 | 41.4 | 0.63 |
| | NWBL-08 | 167.7 | 41.9 | 0.65 | 126.2 | 41.5 | 0.72 |
| | NWBL-13 | 171.4 | 45.6 | 0.73 | 127.9 | 43.5 | 0.71 |
| | NWBL-27 | 180.1 | 54.3 | 0.91 | 134.8 | 45.3 | 0.34 |
| | UL 132 | 202.8 | 77 | 1.37 | 156.4 | 46.5 | |
| | NWBL-31 | 183.6 | 57.8 | 0.98 | 137 | 46.6 | 0.35 |
| | NWBL-17 | 159.7 | 33.9 | 0.49 | 112.3 | 47.5 | 0.31 |
| | BM 7 | 216.6 | 90.8 | 1.97 | 167.1 | 49.6 | |
| | NWBL-07 | 173.7 | 47.9 | 0.77 | 123.8 | 49.9 | 0.88 |
| | NWBL-30 | 200 | 74.2 | 1.31 | 149.8 | 50.2 | 0.68 |
| | NWBL-20 | 175.7 | 49.9 | 0.81 | 124.2 | 51.6 | 0.67 |
| | NWBL-04 | 177.1 | 51.3 | 0.84 | 124.9 | 52.2 | 0.09 |
| | NWBL-25 | 186.9 | 61.1 | 1.04 | 134.3 | 52.6 | 0.29 |
| | NWBL-16 | 202.1 | 76.3 | 1.36 | 146.1 | 56 | 0.67 |
| | NWBL-02 | 187.1 | 61.3 | 1.05 | 128.9 | 58.2 | 0.21 |
| | NWBL-01 | 184.3 | 58.5 | 0.99 | 125.6 | 58.7 | 0.36 |
| | NWBL-03 | 201.7 | 75.9 | 1.35 | 138 | 63.7 | 0.42 |
| | NWBL-24 | 196.8 | 71 | 1.25 | 131.8 | 65 | 0.35 |
| | NWBL-06 | 209.9 | 84.1 | 1.55 | 141.9 | 68 | 0.32 |
| | NWBL-26 | 203.4 | 77.6 | 1.38 | 130.4 | 73.1 | 0.75 |

*Tested in a separate run; dose values calculated from a different calibration curve Δ Rate 2 values (assay signal in the absence of solid-phase antibody minus signal in the presence of antibody) for all true positive samples were >25 mAU/min, while the Δ Rate 2 values for all false positive samples were <15 mAU/min. Taken together, these results demonstrate the ability of the secondary screening test to discriminate between true positive results (due to either parent LSD or to metabolites) from false positive results caused by drug cross-reactants.

For routine use, the LSD secondary screening test is conducted using insolubilized neutralizing antibody that has been aliquoted for individual sample determination (50 μL). The antibody is aliquoted in screw-cap microfuge tubes, and stored at 2–8° C. before use. For each sample of urine testing positive in the CEDIA® DAU LSD assay:

1. Add 500 μL of sample to the LSD secondary screen tube and replace the cap.
2. Mix by mechanical rocker or by inversion for ≧10 min at room temperature
3. Pour the tube (≧200 μL liquid) into a Hitachi automatic analyzer sample cup
4. Let the cup stand at room temp for ≧10 min (to let the resin settle)
5. Perform the standard CEDIA® DAU LSD assay procedure on the processed sample according to the package insert The secondary screen can be conducted without recalibration, providing it is conducted within 48 hours of the direct test and the same reagents are used. Otherwise, the direct test is re-run alongside the confirmatory test. The secondary screening test net rate is the difference between the Δ rate of the untreated sample, and the Δ rate of the treated sample, calculated as indicated above. A net rate of ≧25 is interpreted as a true positive for LSD.

TABLE 5

Scheme for disposition of samples

| Test Performed | Interpretation of Positive result | Interpretation of Negative result |
|---|---|---|
| Initial CEDIA ® DAU LSD assay (Direct Test) | If the ΔRate is positive (but below the upper limit): Proceed to Confirmatory test (If the Δrate is above the upper limit: Proceed to GC/MS) | If the Δ rate is negative: Report sample as negative for LSD |
| Secondary Screening (Confirmatory Test) | If the Secondary Screening test Net Rate is ≧25: Immunoassay positive, proceed to GC/MS | If the Secondary Screening test Net Rate is <25: Report sample as negative for LSD |
| GC/MS (or equivalent) | If the test is positive: Report sample as positive for LSD | f the test is negative: Report sample as negative for LSD |

All publications and patent applications mentioned in this specification are herein incorporated by reference to the same extent as if each individual publication or patent application were explicitly and individually incorporated by reference.

The invention now being fully described, it will be understood that the specification and examples are illustrative but not limiting of the present invention, and that adjustments and modifications will readily be apparent to those skilled in the art without departing from the spirit and scope of the appended claims.

What is claimed as the invention is:

1. An assay method for distinguishing between a small molecule analyte selected from the group consisting of LSD, LSD metabolites, and combinations thereof and an interfering substance in a sample comprising the steps of:
   a) preparing a reaction mixture comprising the sample, a hapten derivative that provides a signal and a detecting antibody that binds with the hapten derivative to yield a detectable signal in the assay, wherein the detecting antibody binds the hapten derivative in a manner that is specifically inhibitable by the analyte;
   b) measuring the amount of the detecting antibody bound to the hapten derivative in step a);
   c) treating the same sample or duplicate thereof with a neutralizing antibody in an amount sufficient to prevent the analyte but not all the interfering substance in the sample from binding the detecting antibody;
   d) preparing a reaction mixture comprising the treated sample or duplicate, a hapten derivative that provides a signal, and a detecting antibody that binds with the hapten derivative to yield a detectable signal in the assay, wherein the detecting antibody binds the hapten derivative in a manner that is specifically inhibitable by the analyte;
   e) measuring the amount of the detecting antibody bound to the hapten derivative in step d);
   f) determining the difference in signal measured in step e) from step b); and
   g) comparing the difference in signals in steps b) and e) to determine (i) the presence of analyte in the sample if the amount measured in step b) is significantly different from the amount measured in step e); or (ii) the presence of interfering substance in the sample if the amount measured in step b) is not significantly different from the amount measured in step e).

2. The assay method of claim 1, wherein the analyte is LSD or an LSD metabolite, and the interfering substance is selected from the group consisting of methamphetamine, fenfluramine, ambroxol, ergotyptine, dihydroergotamine, ecogonine, ergonivine, ergotamine, lysergic acid, lysergol, methysergide maleate, psilocybin, psilocyn, seretonine, tryptophan, fentanyl, 2-oxo-3-hydroxy LSD, and chlorpromazine.

3. The assay method of claim 1, wherein the hapten derivatives of steps a) and d) are each a conjugate in which a hapten is linked to an enzyme, wherein the reaction mixtures of steps a) and d) further comprise a substrate for the respective enzyme, and the measuring in steps b) and e) comprises measuring enzyme catalyzed conversion of the respective substrate to a product.

4. The assay method of claim 1, wherein the hapten derivatives of steps a) and d) are each a conjugate in which a hapten is linked to an enzyme donor; wherein the reaction mixtures of steps a) and d) further comprise both an enzyme acceptor that complements the respective enzyme donor to form an active enzyme when the detecting antibody is not bound to the hapten in the conjugate, and a substrate for the respective active enzymes; and wherein the measuring in steps b) and e) comprises measuring enzyme catalyzed conversion of the respective substrate to a product.

5. The assay method of claim 4, wherein the same conjugate, enzyme acceptor, and substrate are used to form the reaction mixtures of steps a) and d), and the method comprises the step of measuring the relative rate of enzyme catalyzed conversion of the substrate to a product between the two reaction mixtures.

6. The assay method of claim 1, wherein the sample is a urine sample.

7. The assay method of claim 1, wherein the sample is selected from the group consisting of a serum and a plasma sample.

8. The assay method of claim 1, wherein the analyte is LSD and the interfering substance is an LSD metabolite.

9. The method according to claim 1, wherein the detecting antibody is raised against an LSD conjugate derivatized via the N−1 position of LSD.

10. The method of claim 1, comprising removing analyte bound to the neutralizing antibody from the sample or duplicate after the treating of step c) and before the measuring of step e).

11. The assay method of claim 1, wherein the neutralizing antibody is insoluiblized.

12. The assay method of claim 1, which is a homogeneous assay.

13. The assay method of claim 1, wherein the hapten derivatives of steps a) and d) are each a hapten selected from the group consisting of a fluorescent hapten and a fluorescent quench hapten, and the measuring in steps b) and e) comprises measuring a property selected from the group consisting of fluorescence emission and fluorescence polarization.

14. A kit for distinguishing between a small molecule analyte selected from the group consisting of LSD, LSD metabolites, and combinations thereof and an interfering substance in a sample in a confirmatory assay comprising:

a) a detecting antibody that binds with the analyte to give a positive reaction in the assay;

b) a neutralizing antibody that binds with the analyte to prevent the analyte from giving a positive reaction in the assay; and c) a hapten derivative that provides a signal;

wherein the detecting antibody binds the hapten derivative in a manner that is specifically inhibitable by the analyte and the interfering substance; and the neutralizing antibody preferentially binds the analyte in comparison with the interfering substance; and the neutralizing antibody is in an amount sufficient to prevent the analyte in the sample from binding the detecting antibody, but not sufficient to prevent all the interfering substance in the sample from binding the detecting antibody.

15. The kit of claim 14, wherein the analyte has a molecular weight <1,000 daltons.

16. The kit according to claim 14, wherein the detecting antibody is raised against a conjugate in which an LSD derivative is linked to a carrier through a position in the indole ring, and the kit further comprises a conjugate in which an LSD derivative is linked to a carrier through a position in the indole ring.

17. The kit according to claim 16, wherein the neutralizing antibody is raised against a conjugate in which an LSD derivative is linked to a carrier through a position in the indole ring.

18. The kit according to claims 14, wherein the neutralizing antibody is insolubilized.

19. The kit according to claim 18, wherein the detecting antibody and the neutralizing antibody are the same antibody in soluble and insolubilized form, respectively.

20. The kit according to claim 14, wherein the hapten derivative is a fluorescent hapten or a fluorescent quench hapten.

21. The kit according to claim 14, wherein the hapten derivative is a conjugate in which a hapten is linked to an enzyme or enzyme fragment, and the detecting antibody binds the hapten of the conjugate in a manner that is specifically inhibitable by the analyte.

22. The kit according to claim 14, wherein the analyte is LSD or an LSD metabolite, and the interfering substance is selected from the group consisting of methamphetamine, fenfluramine, ambroxol, and chlorpromazine.

23. A kit for adapting an immunoassay for determining a small molecule analyte selected from the group consisting of LSD, LSD metabolites, and combinations thereof in a sample to permit distinguishing between the analyte and an interfering substance wherein the immunoassay is conducted with the following reagents:

a) a detecting antibody that binds with the analyte to give a positive reaction in the assay; and b) a hapten derivative that provides a signal;

wherein the detecting antibody binds the hapten derivative in a manner that is specifically inhibitable by the analyte and the interfering substance;

wherein the kit comprises a neutralizing antibody for the analyte to prevent the analyte from giving a positive reaction in the assay and in an amount sufficient to prevent the analyte in the sample from binding the detecting antibody, but not sufficient to prevent all the interfering substance in the sample from binding the detecting antibody.

24. The kit of claim 23 wherein the analyte has a molecular weight <1,000 daltons.

25. The method of claim 1 wherein the analyte has a molecular weight <1,000 daltons.

26. The kit according to claim 23, wherein the neutralizing antibody is insolubilized.

* * * * *

UNITED STATES PATENT AND TRADEMARK OFFICE
CERTIFICATE OF CORRECTION

PATENT NO. : 6,306,616 B1
DATED : October 23, 2001
INVENTOR(S) : Jeffrey E. Shindelman It is certified that error appears in the above-identified patent and that said Letters Patent is hereby corrected as shown below:

Column 1,
Line 2, the following text is missing: This application is a Continuing Prosecution Application of United States Patent Application Serial No. 09/049,464 filed March 27, 1998.
Line 38, reads "EMIT® = 0 II" and should read -- EMIT® II -- .

Column 2,
Line 19, reads "5.573,955" and should read -- 5,573,955 --.

Column 3,
Line 50, reads "Thus samples" and should read -- Thus, samples --.
Line 55, reads "confirmation test" and should read -- confirmation tests --.

Column 4,
Line 56, reads "confirmatory test" and should read -- confirmatory tests --.

Column 5,
Line 42, reads "graphs compares to the results of the direct (■) and confirmation (♦) test for LSD" and should read -- graphs compare to the results of the direct (■) and confirmation (♦) tests for LSD --.
Line 49, reads "test" and should read -- tests --.
Line 51, reads "methamphetamine:" and should read -- methamphetamine; --.
Line 58, reads "Lower (graphs (left" and should read -- Lower graphs (left --.

Column 7,
Line 32, reads "test" and should read -- tests --.
Line 44, the sentence "The term "enzyme immunoassay" includes ..." should begin a new paragraph.

Column 8,
Line 35, reads "Non limiting" and should read -- Nonlimiting --.
Line 59, reads "a labeling features" and should read -- a labeling feature --.

UNITED STATES PATENT AND TRADEMARK OFFICE
CERTIFICATE OF CORRECTION

PATENT NO. : 6,306,616 B1
DATED : October 23, 2001
INVENTOR(S) : Jeffrey E. Shindelman It is certified that error appears in the above-identified patent and that said Letters Patent is hereby corrected as shown below:

Column 9,
Line 5, reads "at least 99%" and should read -- at least about 99% --.
Line 14, reads "p-hydroxyamphetaminc" and should read -- p-hydroxyamphetamine --.
Line 65, reads "polyacrylamide latex, or" and should read -- polyacrylamide, latex, or --.

Column 10,
Line 50, reads "than that the proportion" and should read -- than that of the proportion --.

Column 11,
Line 19, reads "than that the proportion" and should read -- than that of the proportion --.
Line 45, reads "not necessarily. the" and should read -- not necessarily, the --.

Column 12,
Lines 6 and 15, read "LSD)" and should read -- LSD --.
Line 52, reads "methylamimorpopane" and should read -- methylaminopropane --.
Line 55, reads "metlhamplhetamine" and should read -- methamphetamine --.

Column 13,
Line 25, reads "phosphatic" and should read -- phosphate --.
Line 34, reads "assays using, fluorescent" and should read -- assays using fluorescent --.
Line 51, reads "piperidine))" and should read -- piperidine) --.
Line 55, reads "11:610. 1978" and should read -- 11:610, 1978 --.

Column 14,
Line 67, reads "preceding, paragraph;" and should read -- preceding paragraph; --.

Column 15,
Line 66, reads "this approach the" and should read -- this approach, the --.

UNITED STATES PATENT AND TRADEMARK OFFICE
CERTIFICATE OF CORRECTION

PATENT NO. : 6,306,616 B1
DATED : October 23, 2001
INVENTOR(S) : Jeffrey E. Shindelman It is certified that error appears in the above-identified patent and that said Letters Patent is hereby corrected as shown below:

Column 16,
Line 13, reads "this approach., the" and should read -- this approach, the --.
Line 16, reads "(along) with the analyte)" and should read -- (along with the analyte) --.
Line 45, reads "binding, compound" and should read -- binding compound --.
Line 49, reads "the analyte and" and should read -- the analyte, and --.
Line 64, reads "CEDIA DAU®" and should read -- CEDIA® DAU --.

Column 18,
Line 5, reads "the, column" and should read -- the column --.
Line 40, reads "with a the desired" and should read -- with a desired --.
Line 57, reads "1996:" and should read -- 1996; --.

Column 21,
Line 51, reads "4,256,8344" and should read -- 4,256,834 --.

Column 22,
Line 52, reads "cystic" and should read -- cysteine --.
Line 59, reads "P-galactosidase" and should read -- β– galctosidase --.
Line 60, reads "5,032,503:" and should read -- 5,032,503; --.

Column 23,
Line 2, reads "in (U.S." and should read -- in U.S. --.
Line 3. reads "the analog, in" and should read -- the analog in --.
Line 30, reads "Emits®" and should read -- Emit® --.
Line 41, reads "is provided" and should read -- are provided --.
Line 48, reads "Methamphetaminie" and should read -- Methamphetamine --.

UNITED STATES PATENT AND TRADEMARK OFFICE
CERTIFICATE OF CORRECTION

PATENT NO. : 6,306,616 B1
DATED : October 23, 2001
INVENTOR(S) : Jeffrey E. Shindelman It is certified that error appears in the above-identified patent and that said Letters Patent is hereby corrected as shown below:

Column 25,
Line 20, reads "in automated devices equipped" and should read
-- in automated device is equipped --.
Line 40, reads "The measuring, of" and should read -- The measuring of --.

Column 27,
Line 1, reads "following, structure" and should read --following structure --.

Column 28,
Line 21, reads "incubation any" and should read -- incubation, any --.

Column 30,
Line 4, reads "trilluoroacetate" and should read -- trifluoroacetate --.
Line 66, reads "tell" and should read -- ten --.

Column 31,
Line 6, reads "$NaN_3$ was added" and should read -- $NaN_3$) was added --.
Line 21, reads "methamphetaminie" and should read
-- methamphetamine --.

Column 32,
Line 25, reads "methamphetaminie" and should read -- methamphetamine --.
Line 35, Table 2 "Candidate Antibody (200 µg/ml)" should be
placed to the left of the row 7B3, 2E12, 5D10, etc.

Column 34,
Line 3, reads "phenylpropanolaminie" and should read -- phenylpropanolamine --.
Line 9, reads "neutralizing, antibody" and should read -- neutralizing antibody --.
Line 30, reads "methamphetaminine" and should read -- methamphetamine --.
Line 35, reads "The result of the confirmatory test were" and should read
-- The results of the confirmatory tests were --.

Column 35,
Line 23, reads "isoLSD)" and should read -- isoLSD --.

UNITED STATES PATENT AND TRADEMARK OFFICE
CERTIFICATE OF CORRECTION

PATENT NO. : 6,306,616 B1
DATED : October 23, 2001
INVENTOR(S) : Jeffrey E. Shindelman It is certified that error appears in the above-identified patent and that said Letters Patent is hereby corrected as shown below:

Column 36
Line 6, reads "(7.0 mg," and should read -- (7.0 mg), --.

Column 37,
Line 54, reads "(EDCI)" and should read -- (EDCL) --.

Column 39,
Line 8, reads "10 $\mu$I" and should read -- 10 $\mu$L --.
Line 48, reads "or using or a filter" and should read -- or using a filter --.

Column 40,
Line 43, reads "from the direct and confirmation test are" and should read -- from the direct and confirmation tests are --.

Column 43,
Line 12, Table 5 reads "f the test is negative" and should read -- If the test is negative --.

Signed and Sealed this

Eighteenth Day of February, 2003

JAMES E. ROGAN
*Director of the United States Patent and Trademark Office*